United States Patent [19]
Keeling et al.

[11] Patent Number: 5,859,333
[45] Date of Patent: Jan. 12, 1999

[54] PLANTS AND PROCESSES FOR OBTAINING THEM

[75] Inventors: Peter Lewis Keeling, Ames, Iowa; Joseph Lomako; Dave Gieowar-Singh, both of Miami, Fla.; George William Singletary, Ankeny, Iowa; William Joseph Whelan, Miami, Fla.

[73] Assignees: Zeneca Limited, London, United Kingdom; The University of Miami, Miami, Fla.

[21] Appl. No.: 392,816

[22] PCT Filed: Aug. 26, 1993

[86] PCT No.: PCT/GB93/01821

§ 371 Date: Dec. 18, 1995

§ 102(e) Date: Dec. 18, 1995

[87] PCT Pub. No.: WO94/04693

PCT Pub. Date: Mar. 3, 1994

(Under 37 CFR 1.47)

[30] Foreign Application Priority Data

Aug. 26, 1992 [GB] United Kingdom ............... 9218185

[51] Int. Cl.$^6$ ............... A01H 5/00; C12N 15/12; C12N 15/29; C12N 15/82; C12P 19/04
[52] U.S. Cl. ............ 800/205; 435/69.1; 435/101; 435/172.3; 800/250; 800/DIG. 44; 800/DIG. 55; 800/DIG. 56; 536/23.5; 536/23.6
[58] Field of Search .................. 435/69.1, 101, 435/172.3; 800/205, 250, DIG. 44, DIG. 55, DIG. 56; 536/23.5, 23.6

[56] References Cited

U.S. PATENT DOCUMENTS 5,095,174  3/1992  Vandeventer et al. ............ 800/200

FOREIGN PATENT DOCUMENTS

WO9211382  7/1993  WIPO .

OTHER PUBLICATIONS

Ardila et al, "Potato Tuber UDP–Glucose: Protein Transglucosylase Catalyzes Its Own Glucosylation", Plant Physiol. 99, (1992) ppl. 1342–1347.

Campbell et al, "The amino acid sequence of rabbit skeletal muscle glycogenin", European Journal of Biochemistry, vol. 185, No. 1 Oct (11) 1989 pp. 119–125.

Quentmeier et al, "Purification of an autocatalytic protein–glycosylating enzyme from cell suspensions of *Daucus carota* L.", Planta, 171 (1987) 483–488.

FASEB Journal 1992 FASEB Meeting Apr. 5–9, 1992, vol. 6, No. 4, 26 Feb. 1992, p. A1520, Abstract 3382, Gieowar–Singh, D., et al "Purification of self–glucosylating protein from sweet corn."

FASEB Journal 1991 75th Annual Meeting Apr. 21–25, vol. 5, No. 6, Mar. 19, 1991 p. A1547, Abstract No. 6829, Viskupic, et al, "Molecular cloning of a cDNA encoding rabbit skeletal muscle glycogenin."

Rodriguez et al "Peptide characterization and complementary DNA cloning of glycogenin" Invest. Ophthmol. Visual Sci. Annual Meeting Apr. 30–May 5, 1989, vol. 30, 1989 (3 Suppl.) p. 288 Abstract 30.

Smith et al. 1988. Nature 334: 724–726.

Napoli et al. 1990. Plant Cell 2: 279–289.

Snead et al. 1983. Proc. Natl. Acad. Sci. USA 80(23): 7254–7258.

Viskupic et al. 1992. J. Biol. Chem. 267(36): 25759–25763.

*Primary Examiner*—David T. Fox
*Attorney, Agent, or Firm*—Cushman Darby & Cushman IP Group of Pillsbury Madison & Sutro

[57] ABSTRACT

Plants with an altered starch synthesizing ability are produced by incorporating into the genome of the plant at least one donor gene encoding a starch primer. The starch primer is an enzyme capable of initiating starch synthesis, such as an amylogenin and/or glycogenin. DNA constructs encoding a starch primer are provided, particularly constructs encoding amylogenin from maize.

22 Claims, 9 Drawing Sheets

Enzymes of starch synthesis

PLANTS AND PROCESSES FOR OBTAINING THEM

FIELD OF THE INVENTION

This invention relates to novel plants having an altered ability to synthesise starch, and to processes for obtaining such novel plants.

Starch is an important end-product of carbon fixation during photosynthesis in leaves and is an important storage product in seeds and fruits. Starch comprises up to 75% of the grain dry weight in cereals. In economic terms, the starch produced by the edible portions of three grain crops, wheat, rice and maize, provide approximately two-thirds of the world's food calculated as calories.

Starch is synthesised in the plastid compartment (the chloroplast in photosynthetic cells or the amyloplast in non-photosynthetic cells). The biochemical pathway of starch biosynthesis in leaves has been well-characterised and is shown in FIG. 1. The abbreviations used are: G-3-P, glyceraldehyde-3-phosphate; DHAP, dihydroxyacetone phosphate; $P_i$, orthophosphate; $PP_i$, inorganic pyrophosphate; ADPG/ADPglucose, adenosine diphosphate glucose; ATP, adenosine triphosphate; UDPG/UDPglucose, uridine diphosphate glucose. The reactions are catalysed by the following enzymes: 1) phosphoglycerate kinase/glyceraldehyde-3-phosphate dehydrogenase, 2) triose-phosphate isomerase, 3) aldolase, 4) fructose-1,6-bisphosphatase, 5) hexose phosphate isomerase, 6) phosphoglucomutase, 7) ADP-glucose pyrophosphorylase, 8) starch synthase, 9) UDP-glucose pyrophosphorylase, 10) sucrose phosphate synthase, 11) sucrose phosphatase, 12) orthophosphate/ triose phosphate translocator, 13) inorganic pyrophosphatase.

Knowledge of the pathway in storage tissues was greatly improved following the development of a method for the isolation of intact amyloplasts from wheat endosperm (apRees, 1990) and our recent research with $^{13}C$ labelling studies in wheat and maize (Keeling et al, 1988, Plant Physiology, 87: 311–319; Keeling, 1990, ed. C. D. Boyer, J. C. Shannon and R. C. Harrison, pp.63–78, being a presentation at the 4th Annual Penn State Symposium in Plant Physiology, May 1989). FIG. 2 shows the metabolic pathway of starch biosynthesis in maize endosperm. The abbreviations used are the same as in FIG. 1. The reactions are catalysed by the following enzymes: 1) sucrose synthase, 2) UDP-glucose pyrophosphorylase, 3) hexokinase, 4) phosphoglucomutase, 5) hexose-phosphate isomerase, 6) ATP-dependent phosphofructokinase, 7) $PP_i$-dependent phosphofructokinase, 8) aldolase, 9) triose-phosphate isomerase, 10) hexose-phosphate translocator, 11) ADP-glucose pyrophosphorylase, 12) starch synthase, 13) sucrose phosphate synthase, 14) sucrose phosphatase.

Despite this considerable progress, the first priming molecule(s) responsible for initiating starch synthesis in plants have remained an enigma.

In the animal kingdom, glycogen is deposited rather than starch. It is now well established that glycogen synthesis is initiated on a protein primer which remains covalently attached to the mature macromolecule. Recent work on glycogen deposition has identified a new enzyme: glycogenin or self glucosylating protein (SGP) which acts as a primer. The protein primer serves as the anchor on which the oligosaccharide is constructed and on which glycogen is built (Kennedy et al, 1985, Membranes and Muscle ed. by M. C. Berman et al, IRL Press Oxford/ICSU Press, pp65–84). The linkage between the oligosaccharide and glycogenin involves a novel carbohydrate-protein bond, via the hydroxyl group of tyrosine (Rodriguez and Whelan, 1985, Biochem Biophys Res Commun, 132:829–836). The discovery of glycogenin as a covalent component of the glycogen molecule was followed by the discovery in muscle and other tissues of a glycogen-free form that could be revealed by glucosylation from $^{14}C$-labelled UDPglucose (Rodriguez et al, 1986, Proc 18th Miami Winter Symposium, ICSU Short Reports, 4:96–99). On purification to homogeneity, the protein proved to be autocatalytic. It glucosylates itself and in doing so constructs a maltosaccharide chain on itself that primes glycogen synthesis by glycogen synthase and branching enzyme (Lomako et al, 1988, FASEB J, 2:3097–3103). The self-glucosylating protein (SGP) in muscle is not present as such, but is part of a larger molecule (proglycogen) (Lomako et al, 1990, FEBS Lett, 268:8–12; 1991, FEBS Lett, 279:223–228). The linkage of glycogen to tyrosine in glycogenin has been confirmed by Smythe et al (1988, EMBO J, 7:2681–2686), as has the autocatalytic nature of glycogenin (Pitcher et al, 1988, Eur J Biochem, 176:391–395). The glycogenin protein from rabbit skeletal muscle has been sequenced by Campbell and Cohen (1989, Eur J Biochem, 185:119–125).

The formation of a glycoprotein primer may be a universal feature for the synthesis of polysaccharides. Several proteins have been identified as potential priming molecules for carbohydrate synthesis. None of these proteins, however, has been associated with a polysaccharide macromolecule. Other than mammalian glycogen, the presence of a covalently bound protein (primer) in a mature carbohydrate molecule has yet to be demonstrated.

SUMMARY OF THE INVENTION

According to the present invention there is provided a method of producing a plant with altered starch synthesising ability comprising stably incorporating into the genome of a recipient plant at least one donor gene encoding a starch primer.

This invention is based on our discovery that the enzyme reactions catalyzed by glycogenin are also important in the starch biosynthetic pathway of plant organs. We have identified a new protein responsible for initiating starch synthesis in plants and have named this plant primer enzyme, amylogenin or self-glucosylating protein (SGP). We have therefore redefined the metabolic pathway of starch biosynthesis in plants to incorporate the starch priming reaction catalyzed by amylogenin. FIG. 3 shows the new pathway of starch synthesis in maize endosperm. The abbreviations used are: UDPGppase (UDP-glucose pyrophosphorylase); ADPGppase (ADP-glucose pyrophosphorylase); BSS (bound starch synthase); SSSynthase (soluble starch synthase); BE (branching enzyme).

Starch (amylose and amylopectin) will be synthesized only where the initiator protein (primer) is present and in amounts corresponding to the amount of primer. Amylogenin may determine how much starch is laid down and where it is laid down. It is therefore possible to genetically manipulate the starch content of plants by altering the level and distribution of amylogenin. The genetic manipulation of starch-bearing plants of commercial importance, particularly cereals such as maize, may result in new strains that are advantageous either for direct food uses, or other uses of starch, or as sources of starch to be used as a chemical feedstock. For example, the ratio of amylose and amylopectin in corn starch may be altered which would create starches of considerable utility because of the diverse properties endowed on the different starches as thickening agents, edible food wrapping, etc. This route to new plant varieties complements the traditional and empirical processes of plant breeding.

The basic technology is of potential application to the manipulation of any storage polysaccharide and includes the possibility to suppress polysaccharide synthesis, as well as to enhance it, thereby altering the carbohydrate profile of the plant in directions that may be more favourable for nutritional or industrial uses.

The method according to the invention is generally applicable to all plants producing or storing starch. The recipient plant may be: a cereal, in particular members of the family Gramineae such as maize (corn), wheat, rice, sorghum or barley; a fruit-producing species such as banana, apple, tomato or pear; a root crop such as cassava, potato, yam or turnip; an oilseed crop such as rapeseed, canola, sunflower, oil palm, coconut, linseed or groundnut; a meal crop such as soya, bean or pea; or any other suitable species.

Each donor gene encodes a starch primer (a protein molecule capable of initiating starch synthesis). The primer may be amylogenin and/or glycogenin, including amylogenin of plant origin and/or glycogenin or protoglycogenin of bacterial origin and/or glycogenin of fungal origin and/or glycogenin of animal origin.

A donor gene may be derived from any suitable source including a plant, a bacterium, a fungus or an animal cell. For example, suitable sources of plant genes include plants of the species Zea mays, zea diploperennis, Zea luxurians, Zea perennis, Zea tripsacum, Zea parviglumis, Zea mexicana or teosinte.

A donor gene may be incorporated into the recipient plant genome by sexual crossing of the recipient plant and a sexually compatible donor plant. Alternatively, a donor gene may be isolated and then incorporated into the recipient plant genome by genetic transformation.

The donor gene may be derived from cDNA or genomic DNA (gDNA) encoding a starch primer, or it may be synthesised ab initio using standard techniques. Typically the donor gene encodes the complete primer in the sense orientation so that the transcription product (mRNA) can be translated into the active starch primer enzyme. Alternatively, the donor gene may encode a portion of the starch primer in the sense orientation or may encode some or all of the primer in the antisense orientation so that the transcribed mRNA inhibits expression of the primer enzyme. It is possible to insert more than one copy of the donor gene into the recipient genome. At least one of the donor genes may encode a modified allelic form of the starch primer enzyme having altered characteristics (such as increased or decreased activity, or differing interactions with other enzymes).

It can be seen that the recipient plant's starch synthesising ability may be altered in various ways depending on the particular donor gene(s) which are incorporated. The total amount of starch produced (starch yield) may be increased or decreased; the rate of starch synthesis may be increased or decreased; the starch produced may have an altered structure; the ratio of amylose to amylopectin may be altered; the temperature optimum of starch synthesis may be increased or decreased; the capacity to produce starch at an elevated or lowered temperature may be improved. These effects on starch synthesis are due directly or indirectly to altered activity of the starch primer enzyme(s). For example, interaction of the starch primer enzyme with other starch synthesising enzymes (such as soluble starch synthase or branching enzyme) may affect the degree, rate and/or type of starch production.

To increase the plant's capacity to produce starch, possible methods include:

(1) Increasing the amount of the starch primer enzyme(s) in a recipient plant by the insertion of one or more additional copies of a normal donor gene encoding the primer(s).

The source of these additional copies may be the recipient line itself as the technique would simply increase the amount of enzyme available in the grain rather than change of the properties of the enzyme(s). The gene promoters and other regulatory sequences may also be modified using known techniques to achieve increased amounts of the enzyme in the recipient plant: increased gene expression may be elicited by introducing multiple copies of enhancer sequences into the 5'-untranscribed region of the donor gene.

(2) Insertion of one or more donor genes encoding a starch primer enzyme with enhanced activity.

Achieving this requires the identification of a source of the enhanced activity enzyme gene. Such a source need not be a sexually compatible species as donor genes may be introduced using genetic manipulation techniques. Genetic material may thus be obtained from any source having a primer enzyme with the desired activity characteristics. Exogenous genetic material may alternatively be engineered to give the desired characteristics to the enzymes. Techniques are known in so-called "protein engineering" which can alter the characteristics of an enzyme.

The invention further provides a plant having at least one donor gene encoding a starch primer stably incorporated into the plant's genome such that the plant's ability to synthesise starch is altered. The starch primer may be amylogenin and/or glycogenin.

Presence of the donor gene(s) encoding a starch primer alters the natural process of starch production in the plant. It may alter the rate of starch production, the starch yield, the structure of the starch produced and so on. For example, such transgenic plants may have an increased capacity to produce starch and so are capable of producing higher yields and/or are capable of producing starch at a faster rate. The alteration may be an indirect effect: for example, presence of the donor gene(s) may change the natural expression ratios of the enzymes in the starch biosynthetic pathway leading to altered starch synthesis, including a different amount of starch or a different branching pattern in the starch.

The invention also provides DNA encoding amylogenin and/or glycogenin. Suitable cDNA or gDNA clones may be isolated from cDNA or gDNA libraries using standard cloning techniques. These cDNA or gDNA clones may then be used as probes for equivalent genes in other species, particularly starch-producing organisms. For example, the enzyme amylogenin may be isolated by subjecting a crude plant extract containing the enzyme (eg maize endosperm) to successive purification by gel chromatography. Antibodies to the substantially pure amylogenin protein may be produced. Such antibodies may be used to screen cDNA libraries for the identification of amylogenin clones.

A cDNA clone encoding amylogenin was deposited at the American Type Culture Collection, 12301 Parklawn Drive, Rockville, Md. 20852, U.S.A. under the terms of the Budapest Treaty on 19 Aug. 1993 under the accession number ATCC 69389.

The amylogenin and/or glycogenin DNA clones may be used to alter starch production and starch quality in plants by the method described above. DNA encoding amylogenin and/or glycogenin may be transferred into plants by sexual crossing or by transformation. For example, a transgenic maize plant containing an amylogenin DNA clone may have increased starch yield. In another example, a transgenic maize plant containing anti-sense DNA clones may have decreased starch yield but increased sugar content.

The DNA clones may also be used to express the enzyme amylogenin and/or glycogenin in a biological organism such as *E coli.*

BRIEF DESCRIPTION OF THE DRAWINGS

The present invention will now be described, by way of illustration, by the following examples and with reference to the accompanying drawings of which.

DETAILED DESCRIPTION OF THE INVENTION

1.1 A model for the biogenesis of glycogen in animal muscle

Figure 1:
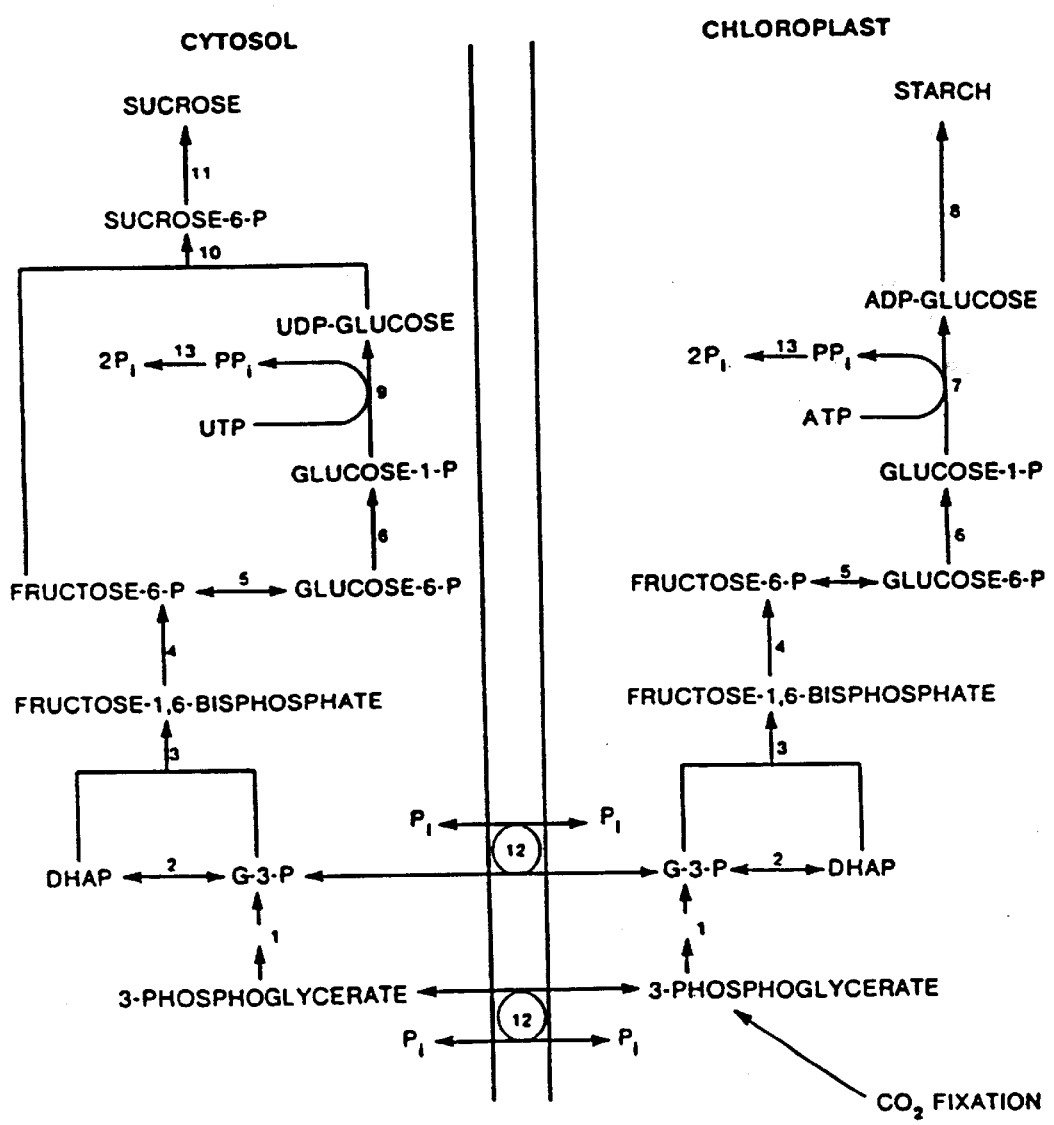
FIG. 1 shows the biochemical pathway of starch biosynthesis in leaves.
Figure 2:
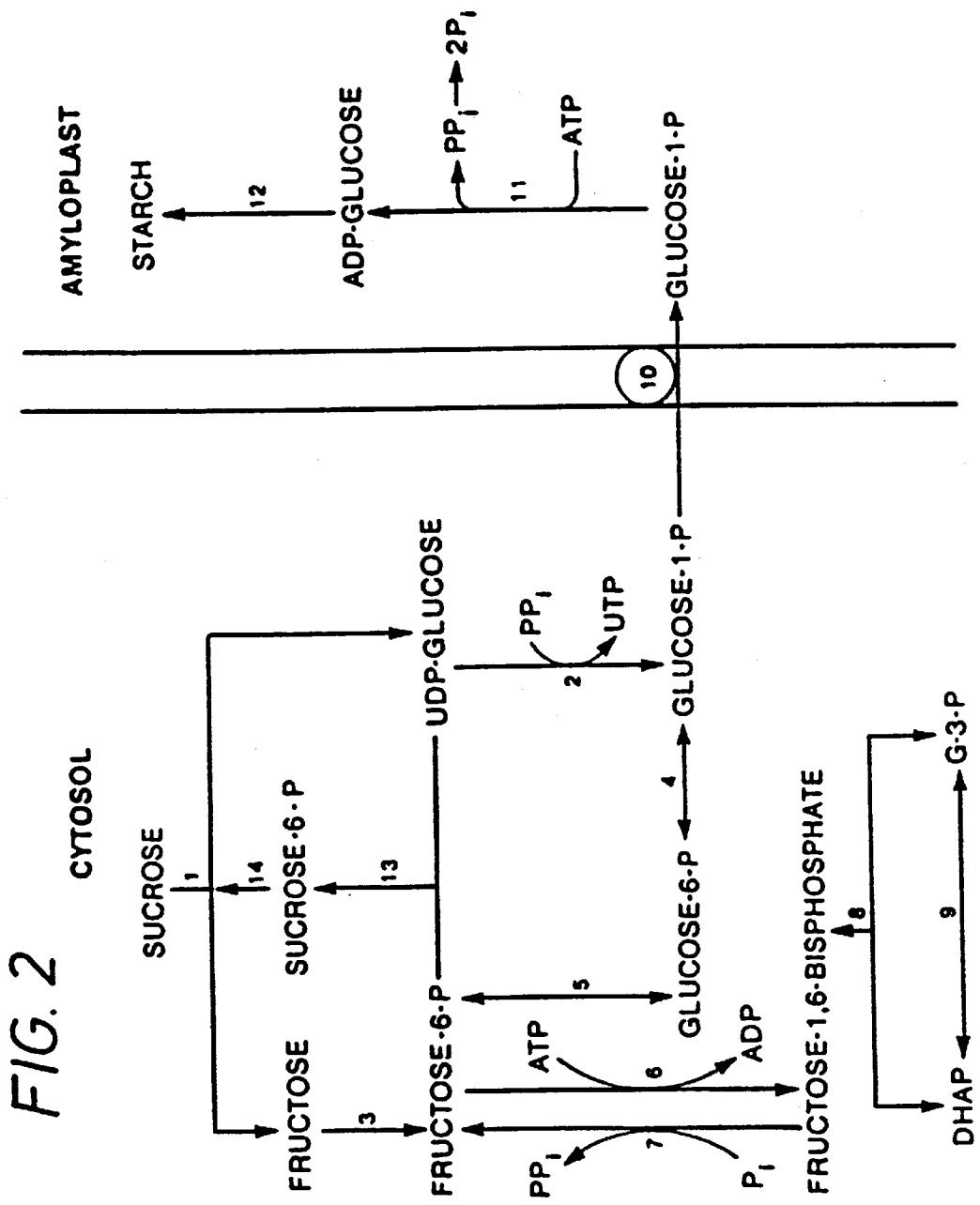
FIG. 2 shows the biochemical pathway of starch biosynthesis in storage tissues.
Figure 3:
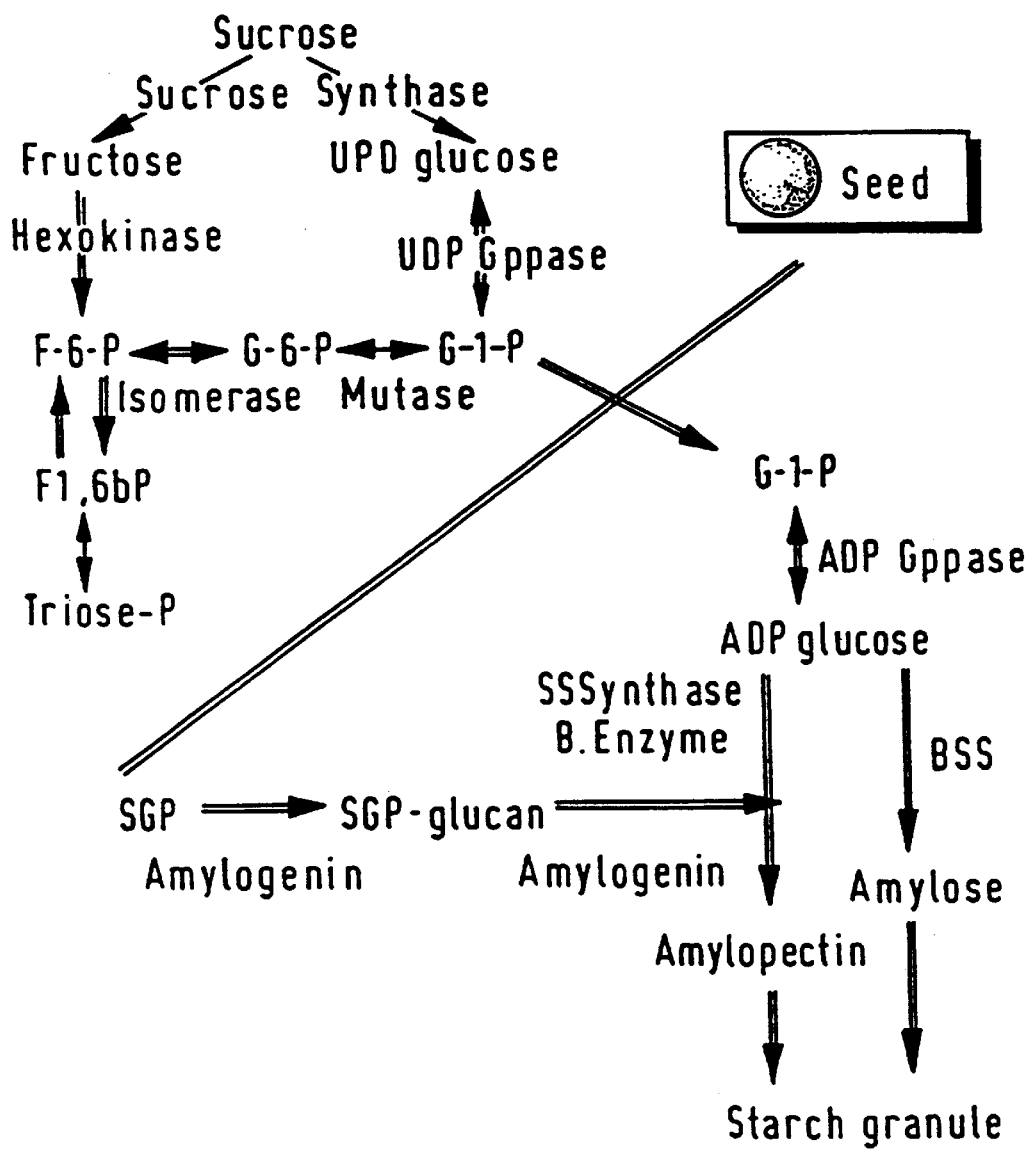
FIG. 3 shows the new biochemical pathway of starch biosynthesis in storage tissues.
Figure 4:
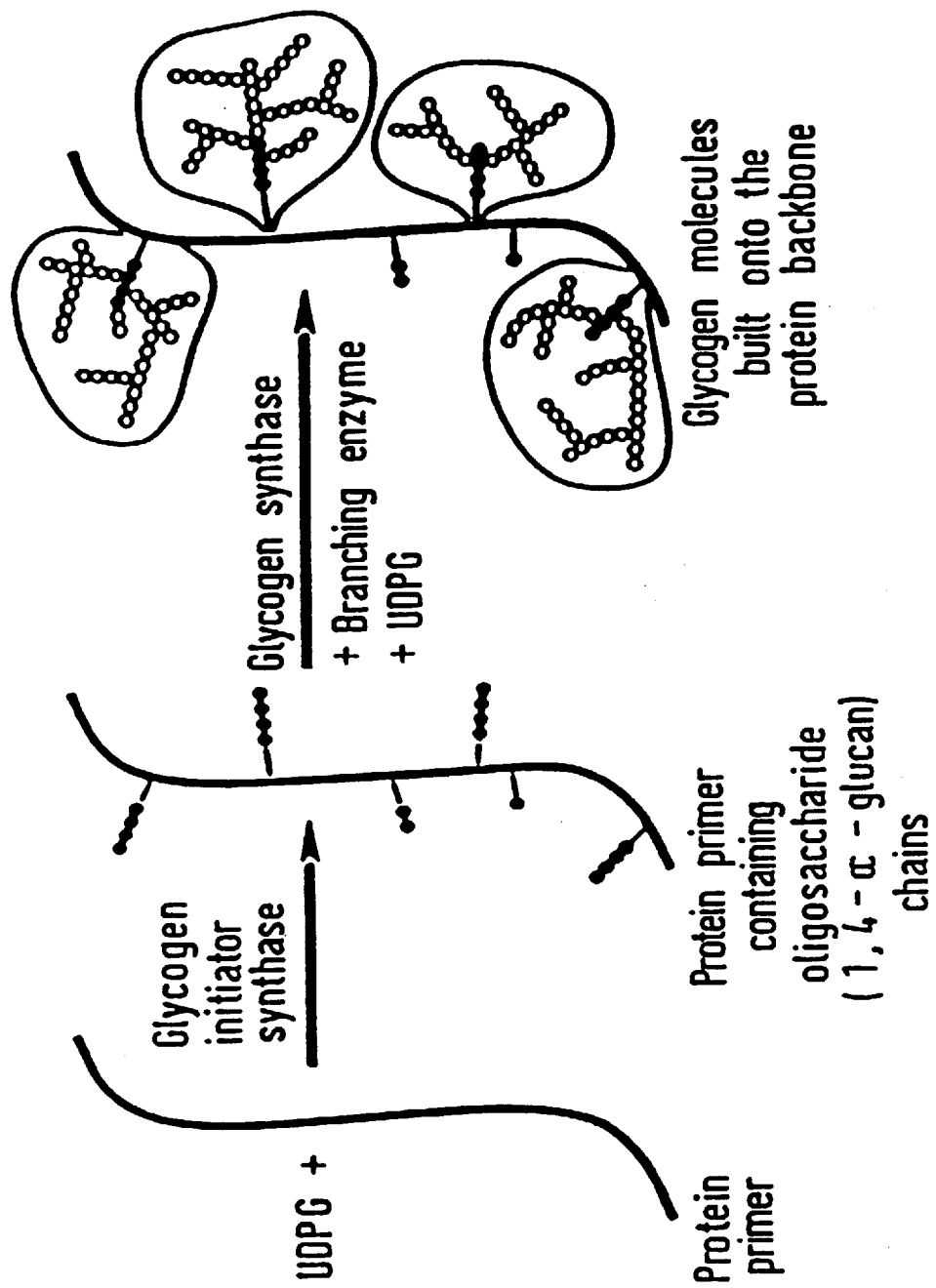
FIG. 4 shows the proposed mechanism of glycogen synthesis.

The proposed mechanism of glycogen synthesis, wherein glucose residues from UDPglucose are first added to the protein primer by glycogen initiator synthase to form oligosaccharide chains that will serve as primers for glycogen synthase and branching enzyme (Krisman and Barengo, 1975), is illustrated in FIG. 4.

Figure 5:
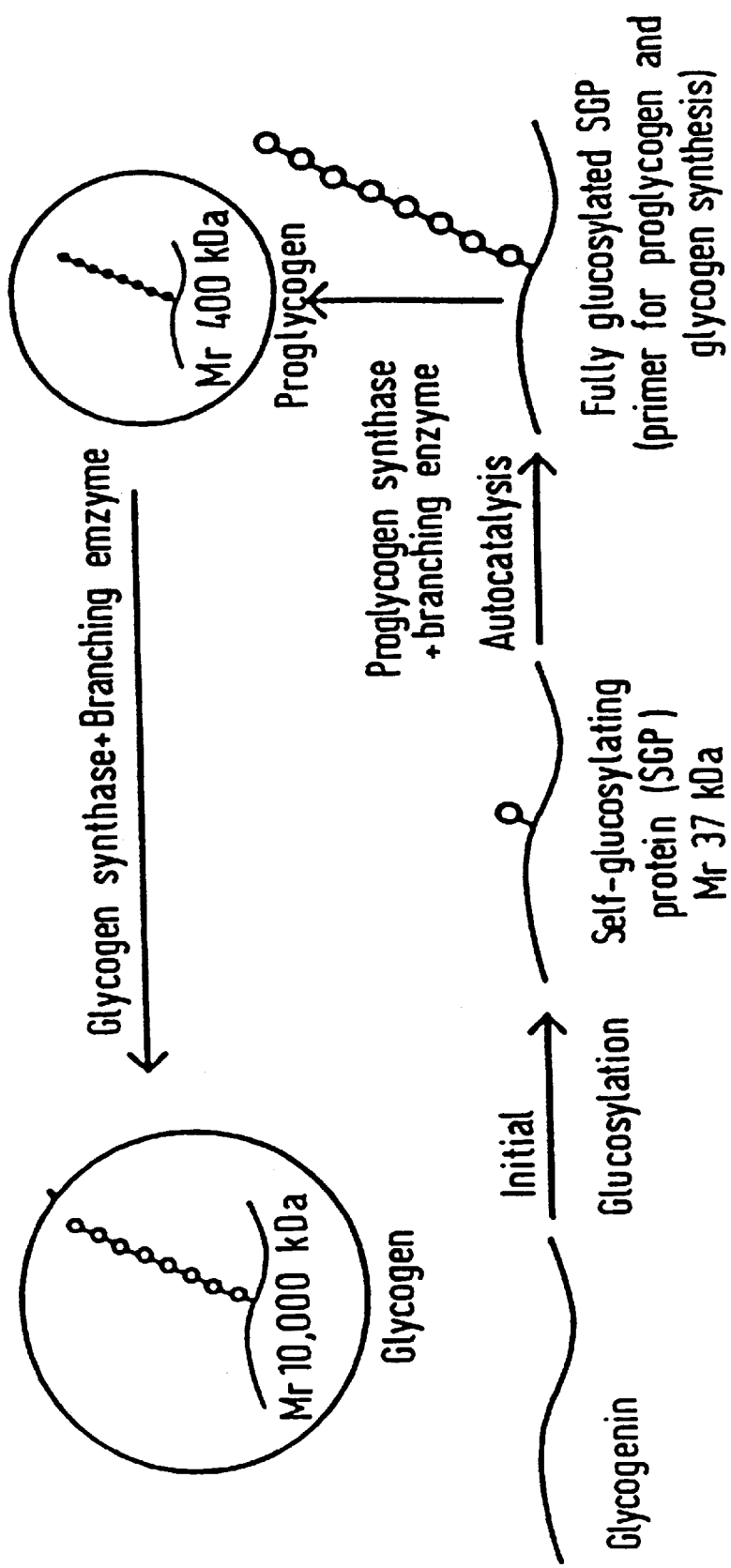
FIG. 5 shows a model for the mechanism of glycogen biogenesis in muscle.

Present knowledge now allows the construction of a model for the mechanism of glycogen biogenesis in muscle which is illustrated schematically in FIG. 5. Following the biosynthesis of the priming protein, namely glycogenin, the first step in the biogenesis of glycogen involves the covalent attachment of glucose to Tyr 194 in glycogenin by a protein tyrosine glucosyltransferase that has yet to be identified. The glucosyl-glycogenin so formed is autocatalytic and extends the covalently attached glucose into a maltosaccharide chain by adding another seven glucose units to itself. Maltooctaosyl-glycogenin then primes the synthesis of proglycogen (Mr 400 kDa) by proglycogen synthase and branching enzyme. Macromolecular glycogen (Mr 10,000 kDa) is synthesized from proglycogen by the classical glycogen synthase with the assistance of a branching enzyme which may or may not be the same as that utilized in the synthesis of proglycogen.

The mechanism of the initial glucosylation of Tyr 194 in glycogenin remains to be elucidated. While a distinct protein tyrosine glucosyltransferase enzyme is envisioned in catalyzing this critical first step, it is possible that glycogenin itself fulfills this role and catalyzes the glucosylation of Tyr 194 before proceeding to elongate the initial glucose unit into a maltosaccharide chain. While the nascent glucose may be extended into a chain of eight glucose residues, proglycogen synthase may act before the chain has reached its full length. In other words, the maltooctaose unit that is constructed on glycogenin after undergoing complete self-glucosylation may not be a prerequisite for the priming of proglycogen synthesis and chains of smaller lengths also may serve as the glucan primer.

The identity of proglycogen synthase also remains to be determined. Whether it is a distinct enzyme or a form of glycogen synthase with a specificity for proglycogen has to be elucidated. If the latter is the case, then the manner in which it differs from classical glycogen synthase will be interesting to examine and may provide additional clues to understanding the intricate regulation of glycogen metabolism.

1.2 A universal mechanism for the biogenesis of polysaccharides

The protein primer model for the biogenesis of mammalian glycogen may extend to starch synthesis and perhaps to polysaccharide synthesis in general. Simple tests using an antibody to glycogenin have indicated that glycogenin-like material may be present in vertebrates, invertebrates, plants, yeast, fungi and bacteria containing glycogen and starch (Gieowar-Singh et al, 1988, FASEB J., 2(1518):A557). The presence of glycogenin-like proteins in a wide variety of lifeforms suggest that similar protein-priming mechanisms for polysaccharide synthesis may be occurring in these species.

The priming mechanism for starch biosynthesis had hitherto not been elucidated and the nature of the priming molecule in vivo remained unknown. However, the present evidence points to a protein primer.

Similar to Krisman's first observation of protein-bound glycogen synthesis with a high speed pellet from a rat liver homogenate, the synthesis of alpha, 1–4 glucan covalently linked to protein was achieved with a potato tuber particulate preparation. A two step mechanism for the formation of the protein-bound alpha, 1–4 glucan in the potato tuber was subsequently proposed. The first step involved the transfer of a glucosyl residue specifically from UDPglucose to an endogenous protein thereby forming a peptidyl-glucose bond. The enzyme that catalyzed the glucosylation was referred to as UDPglucose: protein transglucosylase 1 and it functioned at micromolar concentrations of UDPglucose. In the second step, the glucosylated protein then serves as a primer for the formation of protein-bound alpha, 1–4 glucosidic chains by accepting glucose units transferred from UDPglucose, ADPglucose or glucose 1-phosphate. It was proposed that the chain elongation, which occured in the presence of millimolar concentrations of the glucose donor, was catalyzed by the endogenous starch synthase or phosphorylase in the preparation.

The protein undergoing glucosylation in the first step had a molecular weight of 38 kDa and the added glucose was resistant to hydrolysis by alpha- and beta-amylase. Glucoamylase, however, was capable of hydrolysing the protein-bound glucose which was subsequently identified by paper chromatography. Furthermore, the added glucose underwent beta-elimination upon alkaline treatment in the presence of sodium borohydride and was thereby converted to sorbitol as determined by paper electrophoresis. The conversion of the added glucose to sorbitol implied that the glucosyl moiety was transferred directly to an aminoacyl residue on the acceptor protein and furthermore that the glucan synthesized during the first step consisted of a single glucose unit. In addition, the susceptibility to mild alkaline hydrolysis suggested that the glucose was linked to a serine or threonine residue by an O-glycosidic bond. This was subsequently confirmed by reduction of the beta-elimination products with tritiated sodium borohydride. Tritiated alanine and tritiated 2-aminobutyric acid, expected by $^3$H-sodium borohydride reduction of the 2-amino acrylic acid and 2-amino crotonic acid generated by beta-elimination of carbohydrates attached to serine and threonine residues, were both obtained. Therefore, both serine and threonine residues seemed to be involved in the linkage to glucose.

The ability of the glucosylated protein formed during the first step to serve as a primer for the synthesis of protein-bound alpha, 1–4 glucan was shown by conversion of the former into higher molecular weight material as the attached glucose underwent chain elongation. This was achieved by first allowing the acceptor protein to undergo glucosylation with micromolar concentrations of UDP-[$^{14}$C]glucose during the first step. Unlabelled UDPglucose, ADPglucose or glucose 1-phosphate was then added to the incubation mixture in millimolar concentrations as substrates for the endogenous chain-lengthening glucosyltransferases in the potato tuber preparation.

The increase in the molecular weight of the radioglucosylated protein formed during the first step, was observed by analysis of the final products on urea-SDS-PAGE (sodium dodecyl sulphate-polyacrylamide gel electrophoresis) and fluorography. In addition to the 38 kDa radiolabelled band representing the product formed during the first step a labelled band at 50 kDa was observed on a 12.5% acrylamide gel for the incubation in which unlabelled UDPglucose was added during the second step. When a 10% acrylamide gel was used, the mobility of the band decreased and now migrated to the 70 kDa position. Similar gel patterns were obtained with the incubations in which unlabelled ADPglucose and glucose 1-phosphate were used as substrates for chain elongation.

Fractionation of the solubilized potato tuber preparation on DEAE-cellulose separated the endogenous acceptor protein, which copurified with the enzyme catalyzing its glucosylation during the first step, from the glucosyltransferases that participated in the chain-elongation process in the second step. Furthermore, phosphorylase emerged later than the acceptor protein as two overlapping peaks, each of which also contained starch synthase activity. The glucosyltransferase activities that catalyzed the chain extension of the 38 kDa glucosylated acceptor protein had copurified with the first phosphorylase peak which was used to reconstitute the synthesis of protein-bound alpha, 1–4 glucan. Chain extension was demonstrated by the increase in the molecular weight of the 38 kDa radioglucosylated acceptor protein on SDS-PAGE and fluorography.

The chain lengthening enzymes contained in the first phosphorylase peak utilized UDPglucose, ADPglucose and glucose 1-phosphate as glucosyl donors. Major radiolabelled bands at 43 kDa and 50 kDa were observed on 12.5% acrylamide gels when UDPglucose and ADPglucose were used as chain-lengthening substrates. When glucose 1-phosphate was used, only the 50 kDa labelled band was obtained with the 12.5% gel, which migrated as a 70 kDa species on a 10% gel. The 70 kDa species, following excision and elution from the gel, was partially converted to a species of 38 kDa upon treatment with beta amylase. This supported the contention that the 70 kDa species, or at least part of it, originated from the 38 kDa glucosylated acceptor protein and was synthesized as the latter underwent chain elongation by the addition of alpha, 1–4 glucose moieties.

The enzymic activity that catalyzes the initial glucosylation of the acceptor protein was recently purified. During purification, the glucosyltransferase and the acceptor protein copurified to homogeneity demonstrating that both were one and the same protein. In other words, the glucosyltransferase is an autocatalytic enzyme that undergoes self-glucosylation to form the protein primer required for alpha, 1–4 glucan synthesis in the potato tuber.

A similar autocatalytic glycosyltransferase with a molecular weight of 40 kDa has been purified from Daucus carota L (carrot) cells. The enzyme functions in micromolar concentrations of UDPglucose from which it tranfers glucosyl moieties onto itself. Treatment of the radioglucosylated product with weak alkali (0.1N NaOH, 24° C., 24hr) and strong alkali (1N NaOH/1M NaBH$_4$, 100° C., 10 hr) partially separated the carbohydrate from the protein. Methylation of the oligosaccharides so released produced 2,3,4,6 tetra-O-methyl-glucitol-acetate as the only labelled carbohydrate indicating that autoglucosylation added only one glucose residue to the protein. In addition to UDPglucose, the enzyme also utilized UDPgalactose as a substrate undergoing autogalactosylation. While this carrot enzyme is similar to the autocatalytic protein that appears to prime alpha, 1–4 glucan synthesis in the potato tuber it has yet to be implicated in polysaccharide biogenesis.

The biosynthesis of beta-glucans also appears to proceed through a glycoprotein intermediate. The formation of protein-linked oligosaccharides that seemed to be involved in the synthesis of beta-glucans was detected in bacteria, fungi, algae and higher plants. However, the evidence that a glycoprotein primed beta-glucan synthesis in these studies was circumstantial and a covalent linkage between a beta-glucan chain and a protein was never demonstrated.

In the case of Chlorophyta Prototheca Zopfii (algae) the evidence is more convincing that beta-glucan synthesis is initiated on a protein primer. An intermediate in the synthesis of beta-1,4/1,3-glucan in this alga displayed properties that were consistent with a glycoprotein nature. In addition to being insoluble in trichloroacetic acid, this intermediate was not dialyzable, strongly absorbed at 280 nm and gave a positive reaction with phenol/sulphuric acid, Lowry and Buiret reagents. It contained glucose incorporated from UDPglucose and was shown to be a precursor of alkali-insoluble polysaccharides. This was demonstrated by the synthesis of radiolabelled alkali-insoluble polysaccharides when the radioglucosylated intermediate was incubated with unlabelled UDPglucose and the endogenous enzymes in a fresh membrane preparation of the alga. The polysaccharides so synthesized however seemed to be free of protein indicating that at some point in the elongation process the priming protein was discarded.

This intermediate in beta-glucan synthesis was subsequently isolated and characterized. Membrane preparations from Prototheca Zopfii cells pulsed with [$^{14}$C] proline were incubated with UDP[$^3$H] glucose. The intermediate so formed was double-labelled containing both $^3$H-and $^{14}$C-radioactivity. It was susceptible to partial hydrolysis by cellulase and beta-glucosidase and underwent partial degradation with protease. On gel filtration chromatography, it behaved as a 28000–30000 Da molecule and migrated as a species of the same molecular weight on SDS-polyacrylamide gel electrophoresis. These characteristics firmly established that the intermediate was a glycoprotein with beta-glycosidic bonds in the carbohydrate moiety.

The double-labelled glycoprotein intermediate was resistant to beta-elimination (0.15M NaOH, 1M NaBH$_4$, 100° C., 5 hr) indicating that the carbohydrate moiety was not linked by an O-glycosidic bond to serine/threonine or by an N-glycosidic bond to asparagine. Treatment with saturated barium hydroxide (0.2M Ba(OH)$_2$, 100° C., 6 hr) however, liberated a double-labelled aminoacyloligosaccharide from the glycoprotein. This was consistent with an O-glycosidic linkage to hydroxyproline or hydroxylysine whereby cleavage of the peptide bonds to the glycosylated amino acid occurs. The association of $^{14}$C-label with the liberated oligosaccharide moiety suggested that the carbohydrate was linked to hydroxyproline derived from the radioactive proline that was fed to the cells.

Cellulase digestion of the double-labelled product obtained by barium hydroxide treatment produced a smaller double-labelled aminoacyl oligosaccharide which upon acid hydrolysis and subsequent reduction with tritiated sodium borohydride yielded [$^{14}$C] hydroxyproline and [$^{3}$H] sorbitol. The formation of sorbitol as the only alditol following reduction indicated that glucose was present at the reducing end of the oligosaccharide chain. This suggested that the carbohydrate-protein linkage in the glycoprotein intermediate was an O-glycosidic one between hydroxyproline and glucose.

2. PURIFICATION OF AMYLOGENIN PROTEIN FROM MAIZE ENDOSPERM

The source of the amylogenin enzyme (or self-glucosylating protein, SGP) was a U.S. inbred line (B73) of *Zea mays*.

2.1 Preparation of corn extracts

The kernels were cut from the cobs directly into a food grinder which functioned by continuously extruding the ground material. The ground kernels were collected and expressed through cheese cloth into a beaker surrounded by ice and containing a concentrated extracting solution which, after dilution by the corn juice, gave a final concentration of 50 mM Tris-HCL pH 7.4, 5 mM EDTA (ethylene diamine tetra acetate), 0.1 mM EGTA, 14 mM mercaptoethanol, 0.1 mM PMSF (phenylmethanesulphonyl fluoride), 1 mM benzamidine and 0.1 mg/liter of both leupeptin and pepstatin. Following this, the mixture was centrifuged at 3000×g for 15 minutes at 4° C. and the supernatant retained as the cell-free corn extract.

The amount of concentrated extracting solution needed for each preparation was estimated at the outset. The exact volume of the extract could not be predetermined because of variability in the size of the cobs. Therefore, an average volume of 70 ml of extract/cob was used for estimating the amount of concentrated extracting solution required. After the final volume of the mixture was measured, the quantity of extracting solution was adjusted to give the desired concentration. The use of a concentrated extracting solution facilitated in keeping the volume of the extract to a minimum, which from a typical preparation with 15 cobs of corn, ranged between 1100–1300 milliliters.

2.2 Detection and quantitation of Self-Glucosylating Protein (SGP)

SGP was assayed by incubating a sample of the enzyme with 2 uM UDP-[$^{14}$C]glucose, 5 mM MnCl$_2$ and 50 mM Tris-HCL buffer, pH 7.4 in a 100 ul reaction mixture at room temperature for 30 minutes (the reaction mixture was made up by adding, in the following order, 10 ul each of 10× solutions of Tris-HCL pH 7.4 buffer, MnCl$_2$ and UDPglucose to a 70 ul solution of the enzyme). The reaction was stopped by the addition of 1 ml of 10% TCA (trichloroacetic acid). After standing for 10 minutes the sample was passed through a nitrocellulose filter, type HA 0.45 uM, washed with about 3 ml 10% TCA and approximately 10 ml of water and the filter dried under an infrared lamp. Following this, the filter was placed in 4 ml of scintillation liquid (Ecolume) and measured for $^{14}$C radioactivity in a Searle Delta 300 6890 liquid scintillation counter.

The radioactivity measured on the filter represents $^{14}$C-glucose that was incorporated into TCA-precipitable material (assuming no conversion to the glucose molecule into any other compound). In the case of SGP, which functions by transfering a single glucose residue from UDPglucose onto itself, the assay provides a means of quantitating 'naked' SGP. Endogenously glucosylated SGP would not be detectable and could not be quantitated by this method.

In corn, as in many other plant species possessing SGP-like proteins, the assay also detects, in a crude extract, the incorporation of radioactivity into a TCA-precipitable, lipid-like substance. This lipid-like substance is soluble in methanol, methanol/chloroform and ethanol. In a crude extract of corn, this lipid-like substance represents about 80–90% of the TCA-precipitable, radiolabelled material measured by the assay. As SGP is purified away from this substance, however, the assay provides an accurate measurement of SGP activity.

In a modification of the procedure and in an attempt to measure SGP activity in crude extracts, 1 ml of 95% ethanol was used in place of 1 ml 10% TCA to precipitate protein. After vortexing well to dissolve the lipid-like substance and standing on ice for 30 min to allow protein precipitation, the sample was centrifuged at 7000 rpm for 15 min with a bench top centrifuge. The protein pellet was resuspended in 10% TCA and processed as in the original assay. This provided a way of separating the two activities and allowing SGP activity to be measured in crude extracts.

In addition to scintillation counting, SGP was detected by SDS-PAGE, Western blot analysis and radioautography/fluorography. These procedures, however, were used only for qualitative analyses.

SDS-PAGE was performed with a Mini-Protean 11 electrophoresis system (BioRad) on 10% acrylamide gels according to Laemmli [108]. Samples were electrophoresed in electrode buffer, pH 8.3 (25 mM Tris, 192 mM glycine, 0.001% SDS) with a 25 mA current for approximately 1 hour. Protein bands were visualized by staining gels with either Coomassie blue R-250 or silver (BioRad silver stain kit). Following this, the stained gels were soaked in Amplify for 15 min [109] and dried onto Whatman 3 MM paper in a slab dryer (BioRad) at 60° C.

Western blotting was performed in a Mini trans-blot electrophorectic transfer cell (BioRad). Following SDS-PAGE, proteins from unstained gels were transfered onto nitrocellulose paper in 25 mM Tris, 192 mM glycine, 20% methanol (v/v) pH 8.3 buffer. The transfer was carried out by applying a 150 mA current for 1 hr. After transfer, the nitrocellulose blot was blocked in 5% Carnation lowfat milk dissolved in Tris-buffered saline (20 mM Tris-HCL, 0.5M NaCl, pH 7.4). After blocking, the blot was washed 3 times with Tris-buffered saline (TBS) and then incubated overnight in TBS containing 1% gelatin with goat anti-glycogenin IgG (1:1000 dilution of original stock). Next, the blot was washed 3 times with TBS and then incubated with alkaline phosphatase-conjugated rabbit anti-goat IgG. The antigen-bound protein bands were detected by color development with solutions of BCIP (5-bromo-4-chloro-3indolyl phosphate) and NBT (p-nitroblue tetrazolium chloride) as instructed by the supplier.

Radioautography was performed on dried gels, immunoblots and thin layer silica plates containing radiolabelled materials by exposure to Kodak X-OMAT XAR-5 films at −70° C. (Fluorography was also performed on dried gels in the same manner). The films were developed with an automated Kodak X-OMAT film processor.

2.3 Purification of Self-Glucosylating Protein from Sweet Corn

The following steps were carried out, at 4° C., to obtain homogeneous SGP from sweet corn.

Step 1—Acid precipitation

After preparing a cell-free extract from 15 cobs of sweet corn, the pH was adjusted from 7.4 to 5.0 with 1M ammonium acetate pH 5.0 buffer. Precipitation was allowed to occur for 1 hr. The supernatant, which contained the protein glucosylating activity, was collected by centrifugation at 4000×g for 15 min. Most of the lipid-glucosylating activity remained in the pellet.

Step 2—Fractionation by salt precipitation

Solid ammonium sulphate was added to the pH 5.0 supernatant to give a 50% saturated solution. Protein was allowed to precipitate overnight and collected by centrifugation at 10,000×g. The protein pellet was resuspended in 50 mM Tris-HCL pH 7.4 buffer containing 2 mM CHAPS (TC) and dialyzed against the same buffer. Following dialysis, the solution was centrifuged to remove the considerable amount of undissolved material.

Step 3—Fractionation by ion exchange chromatography

Figure 6:
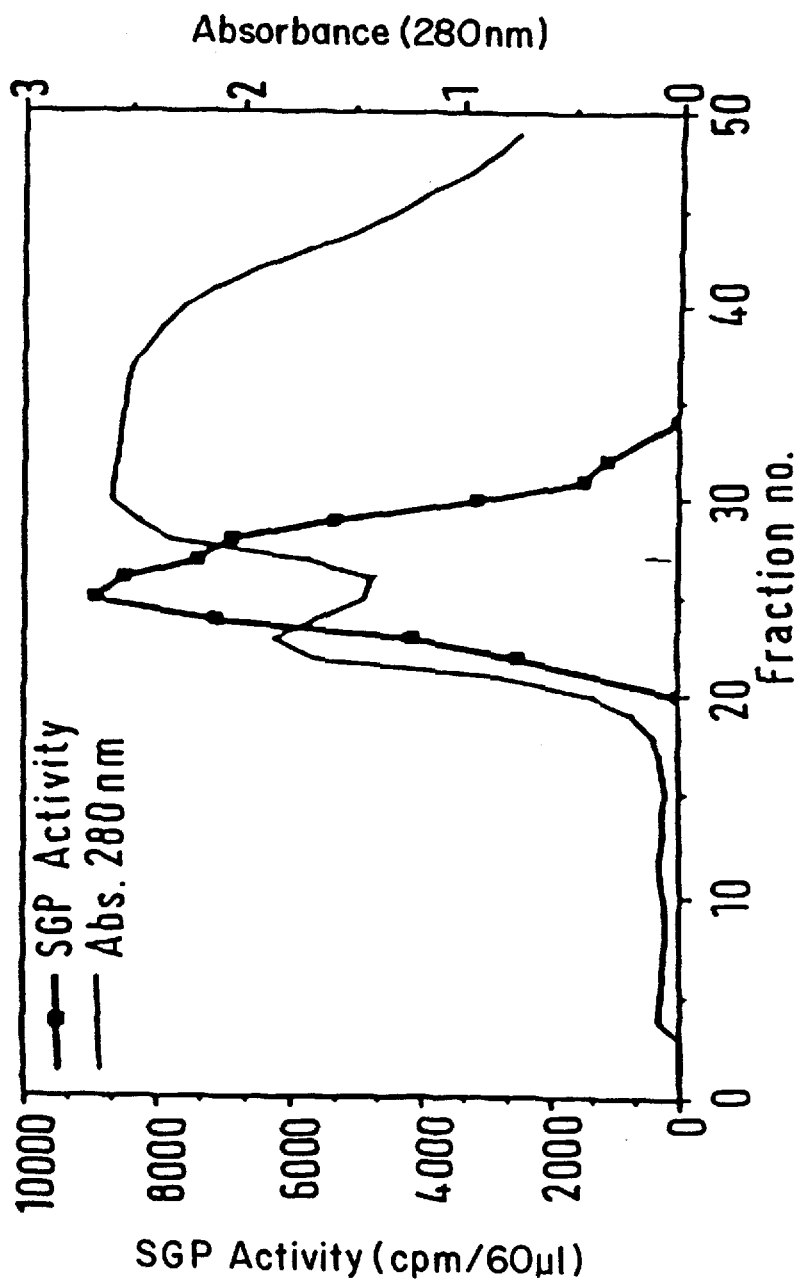
FIG. 6 shows the separation of sweet corn amylogenin (SGP) on DEAE-Sepharose.

The dialyzed solution was applied to a DEAE-Sepharose column (6×15 cm) that was equilibrated with TC. After passing equilibrating buffer through the column to remove unbound material, the protein was desorbed with an increasing concentration gradient of NaCl, from 0 to 1M, formed from 500 ml of TC and 500 ml of TC containing 1M NaCl (FIG. 6). Fractions of 11 ml were collected and assayed for protein-glucosylating activity. The fractions possessing the highest activity were pooled and concentrated to approximately 25 ml by centrifugation using centriprep-10 concentrators (Amicon).

Step 4—Fractionation by gel filtration chromatography

Figure 7:
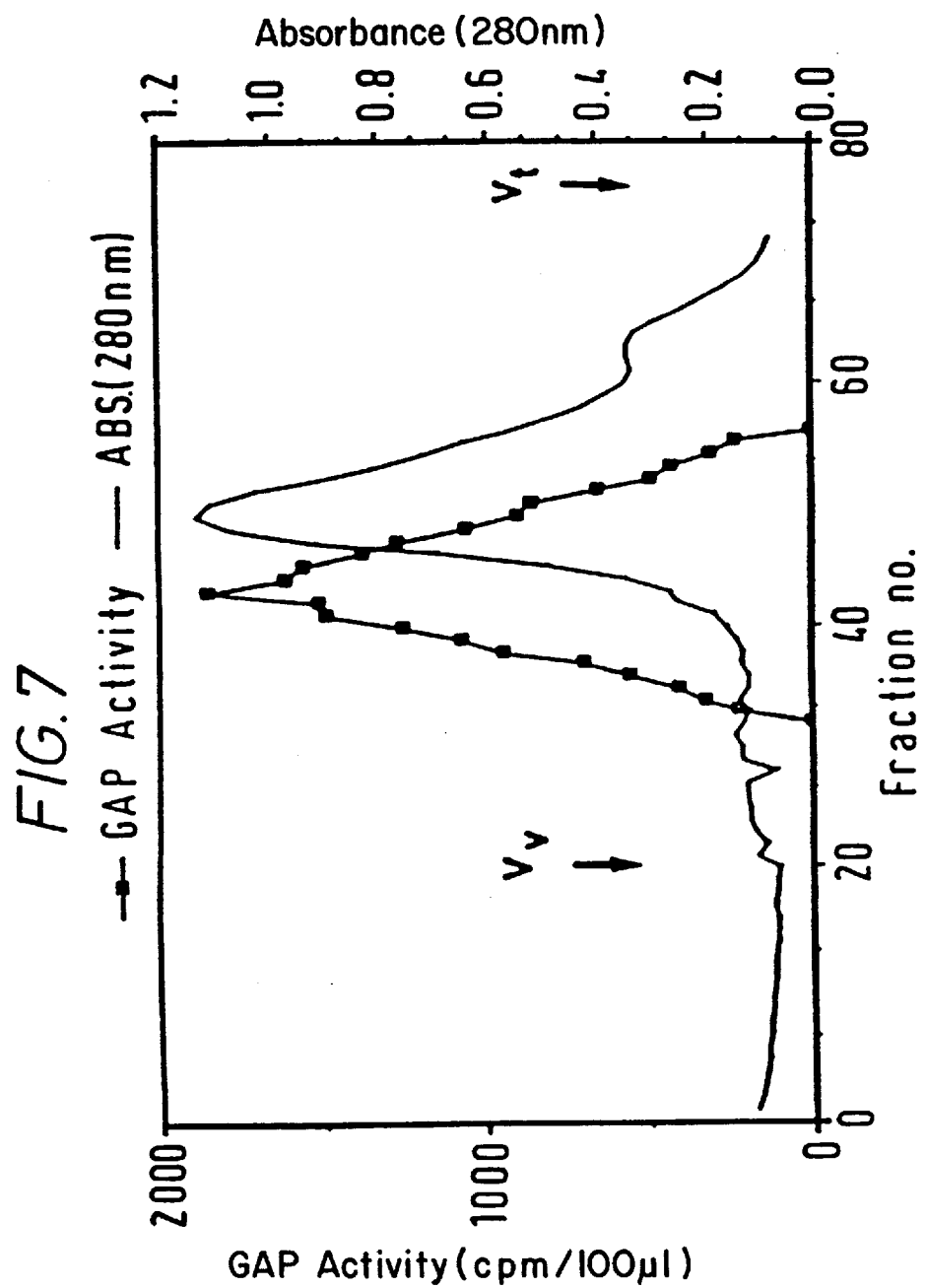
FIG. 7 shows the fractionation of sweet corn amylogenin (SGP) on Sepharose Cl-6B.

The concentrated material was applied, in two equal portions during separate runs, to a Sepharose Cl 6B column (3×85 cm) that was equilibrated with TC and eluted with the same buffer (FIG. 7). The protein-glucosylating activity was found in a single, but broad, peak that began at the void colume. The material that emerged at the front, represented a single protein species on a silver-stained gel after SDS-PAGE and possessed both the glucosylating activity and the glucosylation site. These early fractions containing homogenous protein represented about 10% of the total glucosylating activity applied to the column. The later fractions contained more activity but were increasingly less pure with each additional fraction.

2.4 Purification of Prelabelled SGP from Sweet Corn

The purification of the self-glucosylating protein from sweet corn was accomplished by successive precipitation with acid and salt followed by column chromatography on DEAE-Sepharose and Sepharose C1-6B.

TABLE 1

Purification of sweet corn amylogenin (SGP)

| Purification Step | Specific Activity (×103 cpm/mg protein) | Overall Yield % | Fold Purific'n |
|---|---|---|---|
| crude extract | 5 | 100 | 1.0 |
| pH 5.0 supernatant | 7 | 53 | 1.4 |
| 50% Ammonium Sulphate ppt | 8 | 42 | 1.7 |
| DEAE-Sepharose | 82 | 28 | 16.4 |
| Sepharose | 10700 | 3 | 2140 |

A 3% yield (Table 1) representing approximately 2 nanomoles or 80 ug of the protein was attained from the preparation with 15 cobs of corn. The homogenous SGP so obtained, however, was difficult to process and required additional purification. It appeared that the protein was complexed to lipid. Additional purification to separate the protein away from the contaminating lipid would further reduce the already low yield of the enzyme and therefore, in order to obtain a sufficient quantity of the protein for amino acid and sequence analyses, it was deemed necessary to purify a larger amount of the SGP.

Two approaches were envisioned to obtain an adequate amount of SGP. One was to purify several extracts individually and combine the homogenous protein from each preparation. The other was to purify, in addition to the homogenous protein at the front of Sepharose C1-6B, the impure SGP that elutes later. The first approach was attempted and approximately 4 nanomoles of electrophoretically homogenous SGP was obtained from two preparations with 15 cobs of corn each. In a series of experiments to find an appropriate method to purify the protein from the lipid, most of the material was lost.

In the next attempt to isolate sufficient protein, it was decided to try the second approach by purifying the SGP that elutes later on Sepharose C1-6B together with the portion that emerges at the front as the single protein species. It was not necessary to purify the protein in an active state since the objective was to obtain the amino acid composition and amino acid sequence information on the protein. Therefore, the strategy was to partially purify the SGP, then prelabel the enzyme by allowing it to undergo self-glucosylation and finally isolate the prelabelled protein. The prelabelling of the SGP prevented losses from inactivation of the enzyme during subsequent purification and allowed procedures that involve denaturing conditions to be employed.

The following steps were performed to isolate the self-glucosylating protein from sweet corn in a prelabelled form and was accomplished in two phases.

Phase 1

Partial purification of the self-glucosylating protein and subsequent prelabelling by autoglucosylation:

Step 1—Acid precipitation;

Step 2—Salt precipitation;

Step 3—Fractionation by ion exchange chromatography. Steps 1–3 are exactly the first three steps in the protocol for purifying active SGP (section 2.3) and were carried out in the same manner. Following the fractionation on DEAE-Sepharose and concentration of the SGP containing fractions, the enzyme was allowed to undergo self-glucosylation, 25% with UDP-[$^{14}$C]glucose and the remaining 75% with unlabelled UDPglucose. The prelabelled protein was then purified further.

Phase 2

Purification of the prelabelled SGP:

Step 4—Fractionation by gel filtration chromatography.

Figure 8:
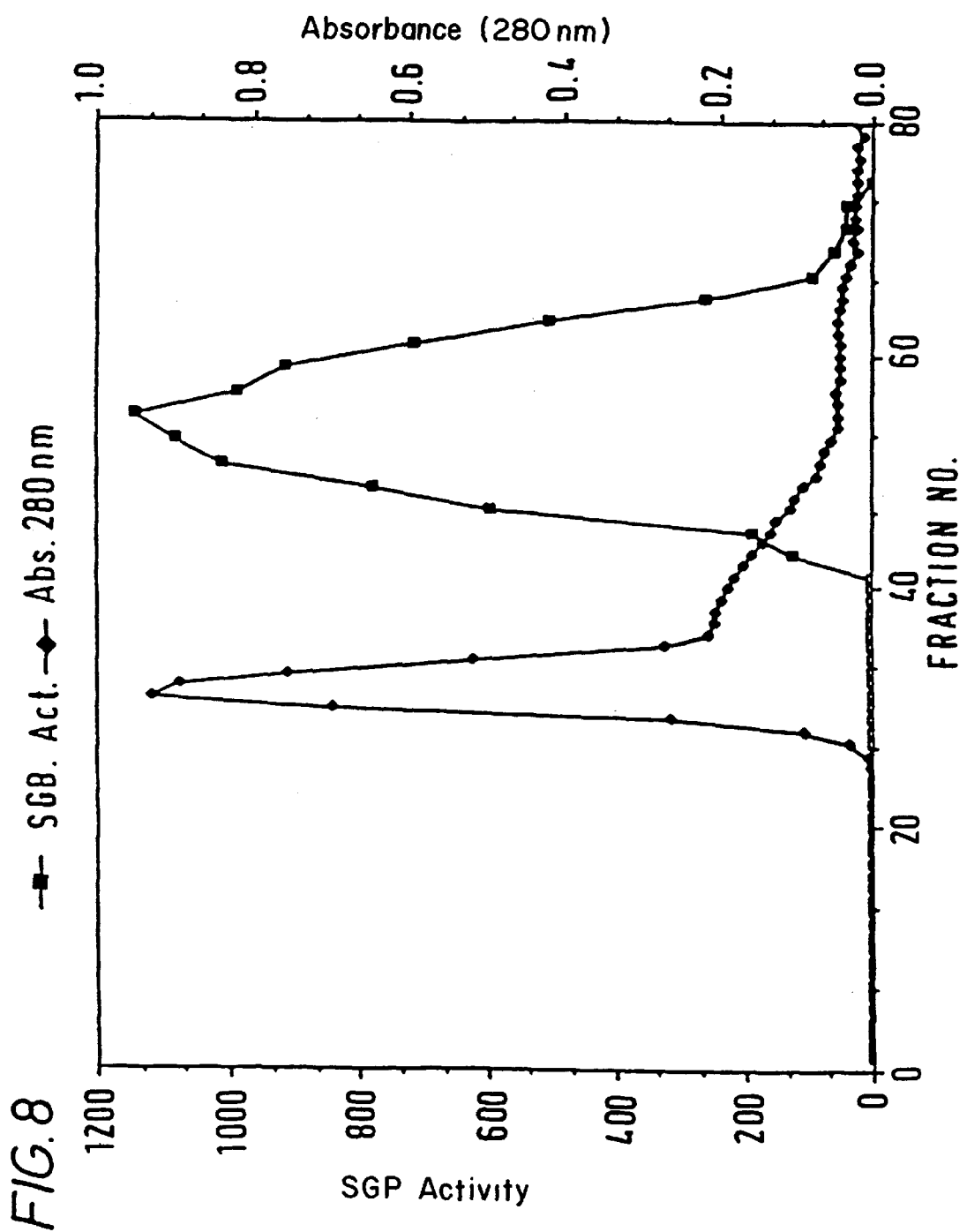
FIG. 8 shows the separation of prelabelled amylogenin (SGP) on Sepharose Cl-6B.

At the end of the prelabelling reaction, the incubation mixture was applied to a Sepharose C1-6B column (3×85 cm) equilibrated with 50 mM Tris-HCL pH 7.4 buffer containing 0.02% triton and eluted with the same buffer (FIG. 8). Fractions were collected in a volume of 5.5 ml each. The prelabelled SGP was detected by measuring 100 ul aliquots from alternating fractions for $^{14}$C-radioactivity. The prelabelled protein emerged in a broad peak similar to that observed for the native unglucosylated enzyme. A peak of $^{14}$C-radioactivity detected at the total volume of the column represented unreacted radiolabelled UDPglucose from the prelabelling reaction.

The purity of the prelabelled SGP was examined by SDS-PAGE in which the protein bands were visualized by silver staining. Fifty microliter (50 ul) aliquots from every third fraction containing prelabelled SGP were analyzed in this manner. The fractions containing the prelabelled protein were then separated into two sets based on their protein content depicted by the silver stained polyacrylamide gel. The earlier fractions (43–51) containing purer SGP were pooled together and the later fractions (52–60) possessing SGP in a less pure state were combined into a second pool. The pools of prelabelled SGP were concentrated by centrifugation using centriprep-10 concentrators (Amicon).

Step 5—Fractionation by Reverse-Phase HPLC.

Following the separation on Sepharose Cl-6B, the prelabelled SGP was purified next by reverse-phase HPLC on a Perkin ELmer HPLC system using a Vydac $C_4$ column (8×40 mm). The sample was fractionated on the column in several portions. During each separation 450 ul aliquots containing 0.26 mg of total protein were applied to the column. This was done to obtain the best resolution of the SGP containing peak. It was observed, during the purification of prelabelled SGP from B73 commercial dent corn, that a larger amount of protein on this column resulted in a lower resolution. The protein was desorbed from the column with linear gradients of acetonitrile generated by using 0.1% TFA (trifluoroacetic acid) in water (solution A) and 0.09% TFA in water containing 84% acetonitrile (solution B) at a flow rate of 1 ml/min. The first two separations were performed successfully with a linear gradient of 0–100% solution B applied over a period of 50 minutes followed by an additional 10 minutes with 100% solution B. In an effort to reduce the time for each run, further separations were carried out with a gradient composed of the following linear segments : 0–30 minutes, 0–70% solution B; 30–31 minutes, 70%–100% solution B; 31–41 minutes, 100% solution B. The altered gradient worked with the same success. Protein was detected by monitoring the absorbance of the effluent at 215 nm and 295 nm simultaneously. Peaks containing protein were collected manually and the prelabelled SGP emerged from the column in a single peak.

Figure 9:
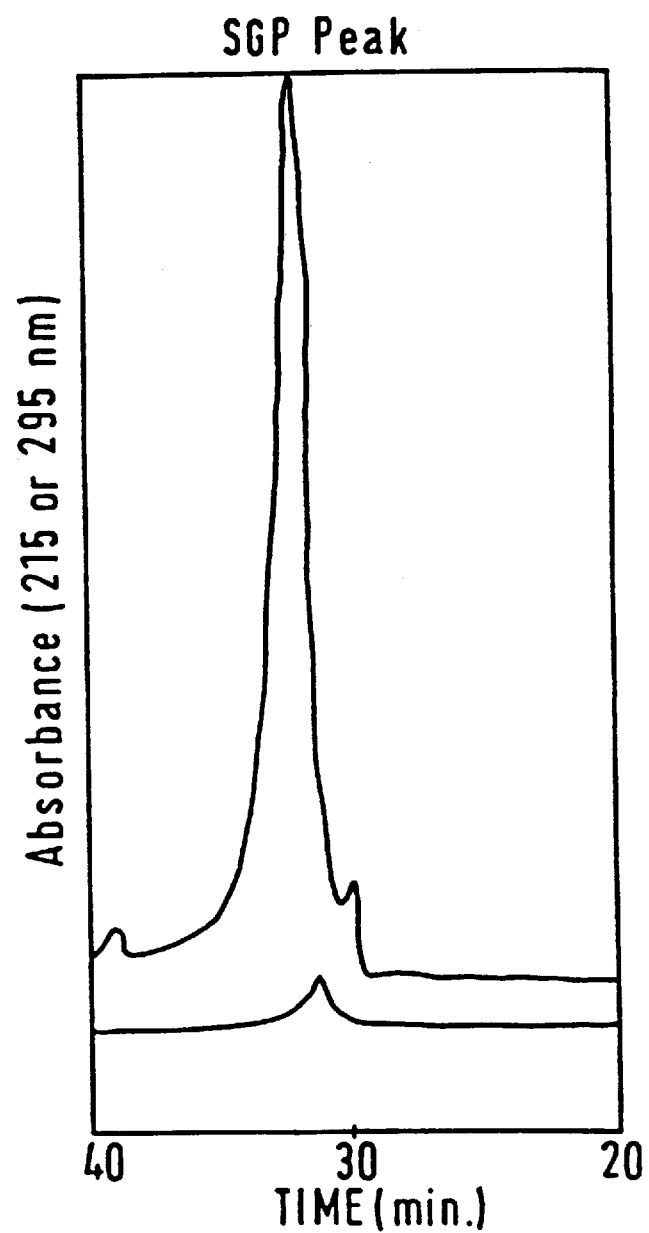
FIG. 9 shows the refractionation of the combined amylogenin (SGP)-containing fractions.

The fractions containing prelabelled SGP from each run were pooled together. The combined fractions had a volume of 10.7 ml and was concentrated to approximately half its volume on a speed-vac. The concentrated sample was then diluted to its original volume with water thereby reducing its acetonitrile concentration by approximately half. The sample was then refractionated on the $C_4$ column in two portions (FIG. 9). In the first run, 5.7 ml of the sample was applied to the column by injecting consecutively six aliquots of 950 ul each. The remainder of the sample was fractionated in a second run by injecting five 950 ul aliquots onto the column. Protein was eluted in the same manner as before and the fractions containing prelabelled SGP from both runs were combined giving a volume of 3.3 ml. Protein determination on the combined fractions by amino acid analysis revealed that 149.2 ug of protein was present. An aliquot containing 3 ug of protein was analyzed on SDS-PAGE for purity. A single homogenous protein band representing prelabelled SGP was observed.

2.5 Reduction and Alkylation of purified SGP

The sample containing 149.2 ug of protein in a volume of 3.3 ml, was prepared for reductive carboxymethylation by adding to it 400 ul of 5M guanidium-HCL, 0.5M Tris-HCL pH 8.6 buffer. After mixing well the solution was concentrated to 0.4 ml on a speed-vac. Reduction and carboxymethylation were performed on the protein in the following manner:

Step 1—Reduction with DTT (20 umol/mg protein).

Five microliters (5 ul) of 1.0M DTT was added to the sample and the reaction tube then flushed with argon. The reaction was allowed to proceed by incubation at 50° C. for 2 hr.

Step 2—Carboxymethylation with iodoacetic acid (60 umol/mg protein).

Next, 15 ul of 1M iodoacetic acid was added and after flushing the tube with argon the sample was incubated at room temperature for 30 min in the dark.

Step 3—Reduction with DTT (30 umol/mg protein).

Seven and one half microliters (7.5 ul) of 1.0M DTT was added to the sample and then incubated at 50° C. for 2 hrs after flushing the tube with argon.

Step 4—Carboxymethylation with iodoacetic acid (60 umol/mg protein).

Next 15 ul of 1M iodoacetic acid was added and the reaction allowed to proceed at room temperature for 30 min in the dark under argon.

The reaction was terminated by adding 17.5 ul of 1.0M DTT to the incubation mixture. Following this, the protein was dialyzed against 50 mM Tris HCL pH 7.6 buffer containing 1 mM $CaCl_2$ on a Pierce Microdialysis System 500. The progress of dialysis was monitored by following the decrease in conductivity of the sample. This was achieved by taking 2.5 ul aliquots from the sample at regular intervals and, after diluting in 10 ml of water, measuring the conductivity. Dialysis was stopped after a 100 fold decrease in conductivity was obtained over 2.5 hr. After dialysis, the volume of the sample had increased to 550 ul and its pH was 7.8.

3. AMINO ACID COMPOSITION AND SEQUENCING OF AMYLOGENIN (SGP)

3.1 Amino acid composition of sweet corn SGP

An accurate determination of the amino acid composition of sweet corn SGP was made by calculating the expected yield of each amino acid after 100 hr of hydrolysis. This was done by performing amino acid hydrolyses on samples of the protein at 110° C. for 24 hr, 48 hr and 72 hr respectively. From a statistical analysis of the yield for each amino acid at each time interval an extrapolation was made for the expected yield at 100 hr and the amino acid composition calculated therefrom. A comparison between the amino acid compositions of sweet corn SGP and glycogenin (Table 2) indicates a general similarity between the two proteins. Other than serine, histidine, threonine and isoleucine, the proportion of each amino acid in the two proteins are comparatively similar. In particular, the ratio of glycine, arginine, alanine, and valine in each protein differ by less than 10% while that of leucine, phenylalanine and lysine are less than 13% different.

TABLE 2

Comparison between the amino acid composition of glycogenin and amylogenin

| Amino Acid | Glycogenin | Amylogenin |
|---|---|---|
| ASX | 1.00 | 1.00 |
| GLX | 0.93 | 0.67 |
| SER | 0.80 | 0.40 |
| GLY | 0.59 | 0.63 |
| HIS | 0.26 | 0.14 |
| ARG | 0.33 | 0.35 |
| THR | 0.84 | 0.44 |
| ALA | 0.59 | 0.65 |
| PRO | 0.44 | 0.60 |
| TYR | 0.26 | 0.37 |
| VAL | 0.63 | 0.67 |
| MET | 0.13 | 0.21 |
| ILE | 0.28 | 0.60 |
| LEU | 0.94 | 0.84 |
| PHE | 0.49 | 0.44 |
| LYS | 0.50 | 0.44 |

3.2 Preparation and isolation of tryptic peptides from purified SGP

The sample of purified prelabelled SGP contained 149.2 ug of protein. On previous occasions, it was found that the partially pure protein was resistant to trypsinolysis with 70% proteolysis occurring over a 48 hr incubation period. To make the purified protein more susceptible to proteolysis, reduction and carboxymethylation was performed. The protein was then digested with trypsin in an enzyme/substrate ratio of 1:25 for 15 hr. The tryptic digest was fractionated on a $C_{18}$ column by reverse-phase HPLC and peptide peaks collected separately. An examination of the fractions for $^{14}$C-radioactivity revealed the presence of 3 radiolabelled peaks.

Nine of the peptide peaks (labelled P1-P9) including the 3 radioactive peaks were further purified by fractionation on a smaller $C_{18}$ column at pH 6.0. Upon refractionation of peaks P1-P9 the following number of tryptic peptides were obtained from each.

| Peak Number | No of tryptic peptide peaks obtained |
| --- | --- |
| P 1 (fraction 29 + 30) | 4 |
| P 2 (fraction 33 + 34) | 3 |
| P 3 (fraction 37 + 38) | 5* |
| P 4 (fraction 42) | 2 |
| P 5 (fraction 54) | 4 |
| P 6 (fraction 55 – 57) | 5* |
| P 7 (fraction 59) | 3 |
| P 8 (fraction 60 + 61) | 1* |
| P 9 (fraction 62) | 1 |

*$^{14}$C-radioactivity containing peaks

The fractionation of P3 and P6 each gave rise to one radiolabelled tryptic peptide peak. The separation of P8, which had very little radioactivity (12000 cpm in total), produced only a single peptide peak which was not radiolabelled. No radioactivity was detected in any of the fractions. It appears that the recovery of radioactivity was too small to be detected.

3.3 Amino Acid Sequence of Tryptic Peptides

An attempt to sequence the N-terminus of sweet corn SGP was made by applying a sample of the purified protein for amino acid sequencing. It was found however that the N-terminus was blocked. Nine of the purified tryptic peptides were chosen for amino acid sequence analyses (labelled T1–T9). The amino acid sequences of these peptides are summarized below.

comprising T2 and T6 formed from incomplete proteolysis. The emergence of the peptide later than T2 and T6 suggest that it has a larger size. The small quantity of radioactivity (12000 cpm ) further suggest that the peptide may have arisen from incomplete hydrolysis and more so that trypsinolysis was performed for only 15 hr. In the amino acid sequence of T2 and T6 no phenylthiohydantoin amino acid was detected at position 7 and 26 respectively and most of the applied radioactivity remained bound to the glass fibre disc, indicating that the [$^{14}$C]-glucosylated amino acid was not extracted by the sequencer solvents. This implied that the radiolabelled glucose was attached to the amino acid at this position.

3.4 Determination of the amino acid involved in the protein-carbohydrate linkage In order to characterize the proteincarbohydrate linkage in the sweet corn SGP, it was necessary to determine the amino acid to which the glucose was attached. This was achieved by performing amino acid analysis and mass spectrometry on the radioglucosylated peptide, T2.

Amino acid analysis of T2 revealed that the peptide had the following empirical composition $D_{1.0}$ $E_{1.0}$ $S_{1.2}$ $G_{2.8}$ $R_{2.0}$ $A_{1.2}$ $P_{nd}$ $Y_{1.1}$ $V_{1.0}$ $L_{1.5}$ (nd=not determined). The composition of the peptide from sequence analysis was $D_1$ $E_1$ $S_1$ $G_2$ $R_1$ $A_1$ $P_1$ $Y_1$ $V_1$ $L_1$ $X_1$. When the two compositions were compared, the most striking difference was in the amount of arginine. Sequence analysis had found only one arginine residue but amino acid analysis indicated that two molecular proportions were present in the peptide. By inference, therefore, the unknown amino acid, X, at position 7 in the peptide must be arginine.

The peptide T2 was submitted to ion-spray mass spectrometry in order to determine its precise molecular mass. The ion-spray mass spectrum of the peptide yielded only one prominant signal at m/z (mass/charge ratio) 888.9 corresponding to a molecular mass of 1777.8 Da for a doubly protonated ion. The molecular mass of peptide T2 calculated from its amino acid composition by assuming an arginine residue in position 7 is 1776.97. By inference, therefore the signal must represent peptide T2 and in combination with the amino acid analysis data confirms that the amino acid to which the glucose is attached at position 7 is arginine. It should be noted that minor signals were observed in the ion spray mass spectrum. These may represent contaminants in the sample as well as sodium and potassium salts of the peptide.

Tandem ion-spray mass spectrometry was also performed on the peptide. A daughter ion spectrum obtained by collisional activation in which the doubly protonated parent ion was bombarded with argon, showed two signals, a prominant one at m/z 889.0 and a minor one at m/z 807.5. The

| | | | | | | | | | | | | | | | | |
| --- | --- | --- | --- | --- | --- | --- | --- | --- | --- | --- | --- | --- | --- | --- | --- | --- |
| T 1 (P 1) (SEQ ID NO: 1) - | Y | V | N | A | V | M | T | I | P | K | | | | | | |
| T 2 (P 3) (SEQ ID NO: 2) - | E | G | A | N | F | V | X | G | Y | P | F | S | L | R | * | |
| T 3 (P 4) (SEQ ID NO: 3) - | Y | X | X | M | W | A | G | W | T | V | K | | | | | |
| T 4 (P 4) (SEQ ID NO: 4) - | E | G | A | H | T | A | V | S | H | G | L | W | L | N | I | P | D | Y | D | A |
| | P | T | Q | L | V | K | P | K | | | | | | | | |
| T 5 (P 5) (SEQ ID NO: 5) - | L | G | D | A | M | V | T | W | I | E | A | W | D | E | L | N | P | S | T | P |
| | A | A | A | D | G | K | | | | | | | | | | |
| T 6 (P 6) (SEQ ID NO: 6) - | L | G | D | A | M | V | T | D | I | E | A | A | D | E | L | N | P | A | G | P |
| | X | X | X | X | K | | | | | | | | | | | |
| T 7 (P 6) (SEQ ID NO: 7) - | N | L | L | S | P | S | T | P | F | F | F | N | T | L | Y | D | P | Y | R | E |
| | G | A | N | F | V | X | G | Y | P | F | S | L | R | * | | |
| T 8 (P 7) (SEQ ID NO: 8) - | G | I | F | W | Q | E | D | I | I | P | F | F | Q | N | V | T | I | P | K |
| T 9 (P 9) (SEQ ID NO: 9) - | N | L | D | F | L | E | M | W | R | P | F | F | Q | P | Y | H | L | I | I | V |
| | Q | D | G | D | P | T | K | | | | | | | | | |

* radioglucosylated tryptic peptides

The radiolabelled peptide T2 is a proteolytic fragment of the larger radiolabelled peptide T6. It is likely therefore that the radiolabelled peptide in P8 was simply a larger peptide major signal represents the doubly protonated parent ion corresponding to the glucosylated peptide T2. The minor signal is due to a doubly charged daughter ion generated by fragmentation of the parent ion. The mass difference between the parent ion and the daughter ion is 163 Da which corresponds to a glucosyl fragment. The presence of only one daughter ion with a loss of a 163 Da fragment from the parent ion strongly suggests that only one glucose residue was attached to the peptide. This implies, therefore, that during the self-glucosylation reaction by the sweet corn SGP only one glucose residue is transferred onto the protein directly to an arginine residue.

3.5 Trypsinolysis of purified SGP

Following carboxymethylation of the purified SGP the protein was digested with trypsin to generate peptides for subsequent sequencing. For this purpose, TPCK-treated trypsin modified by reductive alkylation (Promega) was used. The modified trypsin is extremely resistant to autolytic digestion. The lyophillized TPCK-treated, modified trypsin was dissolved first in 50 mM acetic acid to a concentration of 1 ug/ul. Fifteen microliters (15 ul) of this solution was added to the sample containing 144 ug of purified SGP in a volume of 530 ul giving a protease: protein ratio of 1:25 (w/w). The digest was incubated at 37° C. for 15 hr.

3.6 Purification of Tryptic Peptides from SGP by Reverse-Phase HPLC

The peptides generated by trypsinolysis on purified SGP were isolated by reverse-phase HPLC on a Perkin Elmer HPLC system using a Vydac $C_{18}$ column (100×4 mm). At the end of proteolysis the whole digest was applied to the column. Peptides were eluted with a linear gradient between 0.1% TFA in water (solution A) and 0.09% TFA in water containing 84% acetonitrile (solution B) applied over a period of 100 min at a flow rate of 0.4 ml/min. Peptides were detected by monitoring the absorbance of the effluent at 215 nm and 295 nm simultaneously and collected manually.

Individual peaks were then chosen and purified further by refractionation at pH 6.0 on a smaller $C_{18}$ column (50×2 mm) with the same HPLC system. Each peak was concentrated to half its volume on a speed-vac and then diluted to its original volume with water. This served to reduce the acetonitrile concentration in each sample by approximately half. The samples were refractionated individually by applying each to the $C_{18}$ column. Peptides were eluted from the column with a linear gradient of acetonitrile from 0–84% generated from 10 mM ammonium acetate pH 6.0 and 10 mM ammonium acetate pH 6.0 containing 84% acetonitrile. The gradient was applied over a period of 60 min with a flow rate of 0.15 ml/min. Peptides were detected as before and collected manually. After this round of purification chosen peptides were then subjected to amino acid sequence analyses.

3.7 Amino Acid and Sequence Analyses

Amino acid analyses was performed on both the intact prelabelled SGP and tryptic peptides generated therefrom. This was done by the PTC derivitization procedure on an automated amino acid analyzer. Samples were dried on a speed-vac and then hydrolyzed in 6N HCL at 150° C. for 70 min. Following hydrolysis the samples were dried again on the speed-vac and then 2 nanomoles of norleucine added to each as an internal standard. The samples were then applied to the amino acid analyzer which quantitates the amino acids by reverse-phase HPLC against amino acid standards. The HPLC solutions were 50 mM sodium acetate pH 5.6 (buffer A) and 30 mM sodium acetate pH 4.6 containing 70% acetonitrile (buffer B).

In order to obtain the most accurate amino acid composition of the intact SGP, samples were hydrolyzed in 6N HCL at 110° C. for 24 hr, 48 hr and 72 hr respectively. The amino acid composition was then determined by extrapolation for 100 hr of hydrolysis.

Amino acid sequence analyses were performed by the Edman degradation procedure on an Applied Biosystems 470A gas-phase sequencer equipped with an on line model 120 phenylthiohydantion analyzer using the 03R phenylthiohydantoin standard program.

3.8 Mass Spectrometry and Tandem Mass Spectrometry of Radioglucosylated Tryptic Peptide from Prelabelled SGP Ion-spray mass spectrometry and ion-spray tandem mass spectrometry were performed on the radioglucosylated tryptic peptide isolated from purified prelabelled SGP. The ion-spray mass spectra and ion-spray tandem mass spectra were recorded on a Sciex (Toronto) AP1 111 triple-quadrupole mass spectrometer with 2400-Da mass range equipped with an ion spray source. The mass spectrometer was operated under unit-mass resolution conditions for all determinations. The ion spray voltage was 5 kV.

The samples were dissolved in 1% formic acid/methanol prepared in a 1:1 (vol/vol) ratio and introduced into the ion spray source at a constant flow rate of 5 ul/min with a microliter syringe by using a medical infusion pump (Harvard Apparatus). Argon at a target gas thickness of approximately $1.2 \times 10^{14}$ atoms per $cm^2$ was used as collision gas for tandem mass spectrometry. The collision energies ranged from 40 to 60 eV.

4. NATURE OF THE CARBOHYDRATE COMPONENT OF SWEET CORN SGP

The self-glucosylating protein in rabbit muscle, as isolated, contains at least one glucose unit. Self-glucosylation consists in lengthening this chain to eight units by the addition of 1,4-linked alpha-glucose residues. The added glucose residues are therefore removable by glycogenolytic enzymes. In an attempt to characterize the carbohydrate component of the sweet corn SGP the following studies were performed.

4.1 Acid hydrolysis of prelabelled SGP

The first step was to determine whether the radioactivity incorporated into the SGP was in fact radiolabelled glucose and not a byproduct of a conversion reaction. To examine this, SGP was allowed to undergo radiolabelling and then acid hydrolysis performed on the product. An autoradiograph of the hydrolysate after thin layer chromatography included a radiolabelled glucose standard. Under mild hydrolysis, after boiling in 2M trifluoroacetic acid for 30 minutes, a faint radiolabelled band is seen at the position of glucose. In addition, three slower moving radiolabelled bands of stronger intensity were observed. Under stronger conditions, by boiling for 2 hrs, the same radiolabelled bands are observed. Now, however, the radiolabelled band at the position of glucose was much more intense and the two other bands had a slightly less intensity than before. The appearance of the radiolabelled band at the glucose marker after acid hydrolysis indicates that the radioactivity incorporated into SGP is radiolabelled glucose. Furthermore, the incorporated glucose was not bound by an acid labile bond since strong acid hydrolysis was necessary to release a significant amount of the carbohydrate from the protein. It is unclear what the slower moving radiolabelled bands represent, but perhaps these may be radiolabelled peptide fragments from the protein. The marginally lighter intensity observed for strong acid hydrolysis supports this hypothesis.

4.2 Digestion of prelabelled SGP with glycogenolytic enzymes

The radiolabelled glucose attached to SGP after undergoing radioglucosylation is not removable by glycogenolytic enzymes, namely alpha-amylase, beta-amylase and glucoamylase. It is removable, however, by beta-glucosidase. When a sample was incubated with beta-glucosidase only 50% of the radiolabelled glucose was removed, and only after 72 hr of digestion. The difficulty in hydrolysing the glucose by beta-glucosidase suggested that there may be steric hindrance to the enzyme. Therefore, it was decided to test the beta-glucosidase on a prelabelled tryptic peptide. When this was done, beta-glucosidase removed all the $^{14}$C-labelled glucose from the radiolabelled tryptic glucopeptide isolated from the prelabelled SGP. Alpha-Glucosidase failed to remove any glucose from the same glucopeptide and in the intact prelabelled SGP.

The inability of alpha-amylase, beta-amylase and glucoamylase to remove the added glucose to SGP indicated that multiple alpha-glucose residues were not attached to the protein. The removal of the glucose by beta-glucosidase indicates that it is attached via a beta-linkage. These data, in combination with other analyses, suggest that the glucose is attached in a beta-linkage to an arginine residue on the protein.

4.3 Beta-elimination of radioglucosylated SGP

The alkaline borohydride procedure which beta-eliminates carbohydrate attached to serine or threonine residues on proteins was attempted on radioglucosylated SGP from sweet corn. In this experiment prelabelled SGP from rabbit heart was used as a control since its carbohydrate is attached to tyrosine. Surprisingly, the glucose attached to both the sweet corn and heart proteins beta-eliminated or appeared to do so. After 42 hr of incubation, 63% of the radiolabel from the sweet corn protein and 89% from the heart protein became TCA-soluble. This observation suggested that solubilization of the radiolabel in TCA occurred not by beta-elimination but perhaps by fractionation of the protein into TCA-soluble peptides. It was concluded, therefore, that the conditions of this procedure were to strong for the two proteins.

A second procedure commonly used for beta-elimination by incubation in 0.5M NaOH for 24 hr at 4° C. was performed on the sweet corn SGP. In this case, the glucose attached to the protein failed to beta-eliminate suggesting that the carbohydrate was not attached to a serine or threonine residue. This result is consistent with the finding that the glucose is attached to an arginine residue.

4.4 Acid hydrolysis and Thin Layer Chromatography of Prelabelled SGP

A sample of prelabelled SGP from sweet corn was prepared by allowing the enzyme to undergo self glucosylation with UDP-[$^{14}$C]glucose. This was accomplished by incubating 250 ul of a 16 fold purified sample of the protein with 50 mM Tris-HCl pH 7.4 buffer, 5 mM MnCl$_2$ and 2 uM UDP-[$^{14}$C]glucose in a 500 ul reaction mixture at room temperature for 30 min. The reaction was stopped by extensive dialysis of the incubation mixture against 20 mM Tris-HCl pH 7.4 buffer containing 2 mM CHAPS. Two aliquots of the prelabelled protein (12000 cpm each) were each precipitated with an equal volume of 20% TCA and the pellets collected by centrifugation. The precipitates were washed twice in ether to remove residual TCA. After drying in air, 1.0 ml of 2M trifluoroacetic acid was added to the precipitates. For mild hydrolysis one sample was heated for 30 minutes in a boiling water bath. For strong hydrolysis the other sample was heated for 2 hr instead. Following hydrolysis, the samples were lyophilized and redissolved in 100 ul of water.

After hydrolysis, 10 ul of each hydrolysate was spotted on thin layer silica plates (the plates were heated to 60° C. for about 5 mins to remove moisture before use). After drying, the plates were placed in tanks containing a solvent composed of butanol, water and ethanol in a ratio of 5:4:5. After 24 hr the plate was taken out, dried in an oven and then replaced for a second run. After an additional 24 hr the plate was taken out dried and placed for radioautography.

4.5 Digestion of Prelabelled Sweet Corn SGP with Glycogenolytic Enzymes

A sample of prelabelled SGP from sweet corn was prepared. Five hundred microliters (500 ul) of a 16 fold purified sample of the protein was allowed to self glucosylate with UDP[$^{14}$C]glucose in a 1000 ul reaction mixture. The prelabelled SGP so formed was used in the following digestions.

4.5.1 Alpha-Amylase Digestion

Three hundred microliters (300 ul) containing 22680 cpm of prelabelled SGP was incubated with 100 mM sodium acetate pH 7.0 buffer, 10 mM CaCl$_2$ and 2 U of alpha-amylase in a 400 ul reaction mixture at room temperature. Hydrolysis of glucose attached to the SGP was monitored by measuring any loss of TCA precipitable counts. One hundred microliter (100 ul) aliquots were taken at 1 hr, 3 hr and 18 hr time intervals and precipitated with 1 ml of 10% TCA. The precipitate was filtered on nitrocellulose, washed and measured for $^{14}$C radioactivity.

4.5.2 Beta-Amylase Digestion

Three hundred microliters (300 ul) containing 22680 cpm of prelabelled SGP was incubated with 100 mM sodium acetate pH 5.0 buffer and 0.5 mM dithiothreitol with approximately 2 U of beta-amylase in a 400 ul reaction mixture at room temperature. Hydrolysis of glucose attached to the SGP was monitored in exactly the same manner as described before.

4.5.3 Glucoamylase Digestion

Three hundred microliters (300 ul) containing 22680 cpm of prelabelled SGP was incubated with 100 mM sodium acetate pH 5.0 buffer and 4 U of glucoamylase in a 400 ul reaction mixture at room temperature. Hydrolysis of glucose attached to the SGP was monitored in exactly the same manner as described before.

4.6 Digestion of Prelabelled Muscle SGP with Glycogenolytic Enzymes

This experiment was performed as a control for the glycosidase digestion of prelabelled sweet corn SGP. A sample of prelabelled SGP from rabbit muscle was prepared in a similar manner to that from sweet corn. Two hundred microliters (200 ul) of a 20 fold purified sample of the muscle enzyme was allowed to undergo autoglucosylation in a 400 ul reaction mixture for this purpose. The prelabelled muscle SGP was incubated with glycogenolytic enzymes in the following digestions.

4.6.1 Alpha-Amylase Digestion

Fifty microliters (50 ul) containing 4907 cpm of prelabelled muscle SGP was incubated with 100 mM sodium acetate pH 7.0 buffer, 10 mM CaCl$_2$ and 2 U of alpha-amylase in a 100 ul reaction mixture at room temperature. Hydrolysis of glucose attached to muscle SGP was monitored by loss of TCA precipitable counts. After 18 hr of incubation the entire digest was precipitated with 1 ml of 10% TCA. The precipitate was filtered on nitrocellulose, washed and measured for $^{14}$C radioactivity.

4.6.2 Beta-Amylase Digestion

Fifty microliters (50 ul) containing 4907 cpm of prelabelled muscle SGP was incubated with 100 mM sodium acetate pH 5.0 buffer and 0.5 mM dithiothreitol with approximately 2 U of beta-amylase in a 100 ul reaction mixture at room temperature. Hydrolysis of glucose was monitored in exactly the same manner as described before.

4.6.3 Glucoamylase Digestion

Fifty microliters (50 ul) containing 4907 cpm of prelabelled muscle SGP was incubated with 100 mM sodium acetate pH 5.0 buffer and 4 U of glucoamylase in a 100 ul reaction mixture at room temperature. Hydrolysis of glucose was monitored in exactly the same manner as described before.

4.7 Digestion of Prelabelled SGP with alpha-and beta-Glucosidase

Prelabelled SGP was prepared from 500 ul of a16 fold purified sample of the enzyme in a 1000 ul reaction mixture and used for the following digestions.

4.7.1 Alpha-Glucosidase Digestion

Three hundred microliters (300 ul) containing 25400 cpm of prelabelled SGP was incubated with 100 mM sodium phosphate pH 7.0 buffer and 5 U of alpha-glucosidase at room temperature. At 18 hr, 48 hr and 72 hr time intervals, 100 ul aliquots of the digest were taken and precipitated with 1 ml 10% TCA. The precipitate was filtered on nitrocellulose, washed and counted for $^{14}C$ radioactivity.

4.7.2 Beta-Glucosidase Digestion

Three hundred microliters (300 ul) containing 25400 cpm of prelabelled SGP was incubated with 100 mM sodium acetate pH 5.0 buffer and 5 U of beta-glucosidase at room temperature. One hundred microliter (100 ul) aliquots were taken from the digest at 18 hr, 48 hr and 72 hr time intervals and precipitated with 1 ml 10% TCA. The precipitate was filtered on nitrocellulose, washed and counted for $^{14}C$ radioactivity.

4.8 Digestion of Radioglucosylated Tryptic Peptide from SGP with alpha- and beta-glucosidase

4.8.1 Trypsinolysis of Partially Purified Prelabelled SGP

A radiolabelled tryptic peptide was prepared from prelabelled SGP, obtained with a 16 fold purified sample of the enzyme in the following manner. Three hundred microliters (300 ul) containing 25400 cpm of the prelabelled protein was precipitated with an equal volume of 20% TCA and collected by centrifugation. After washing the pellet twice with ether, it was dissolved in 50 ul of 8M urea containing 0.4M ammonium bicarbonate at pH 8.0. The sample was heated at 55° C. for 15 min and then diluted to 200 ul with water. TPCK-trypsin (Pierce) was then added to the sample to give a 1:25 protease:protein ratio and incubated at 37° C. for 24 hr. Following this, the same amount of trypsin was added again and the sample incubated for a second 24 hr period.

4.8.2 Recovery of Radioglucosylated Tryptic Peptide

After incubation was completed, the tryptic digest was applied to a Biogel P-4 column (80×0.8 cm) equilibrated with 50 mM ammonium bicarbonate buffer and eluted with the same buffer. Fractions of 0.5 ml were collected and 50 ul aliquots taken for measurement of $^{14}C$-radioactivity.

4.8.3 Enzyme Hydrolysis of Radioglucosylated Tryptic Peptide

Samples of the radioglucosylated tryptic peptide (5350 cpm each) were digested with alpha-and beta-glucosidase separately, and each digest fractionated on the same P-4 column. Fractions of the same size as in (b) were collected and measured for $^{14}C$-radioactivity.

4.9 Beta-elimination of prelabelled SGP

Two procedures for beta-elimination of carbohydrate from serine/threonine linked proteins were performed on prelabelled SGP from sweet corn.

4.9.1 Procedure 1

In this procedure, 210 ul containing 15321 cpm of prelabelled SGP from sweet corn (prepared from 16 fold purified enzyme) was incubated with 0.2M sodium hydroxide and 0.3M sodium borohydride in a 300 ul digest at 45° C. Beta-elimination of glucose was determined by measuring any loss of TCA precipitable counts. At 15 hr and 42 hr time intervals 150 ul aliquots were taken and precipitated with 1 ml of 20% TCA. The precipitate was filtered on nitrocellulose, washed with 10% TCA and water and the filter paper measured for $^{14}C$-radioactivity. As a control, 155 ul containing 15213 cpm of prelabelled SGP from rabbit heart (prepared from 20 fold purified enzyme) was incubated with 0.2M sodium hydroxide and 0.3M sodium borohydride in a 300 ul digest at 45° C. Beta elimination of glucose was determined in exactly the same manner.

4.9.2 Procedure 2

A sample containing 200 ul of prelabelled SGP (14591 cpm) from sweet corn, prepared from 16 fold purified enzyme was precipitated with an equal volume of 20% TCA. The pellet was collected by centrifugation and washed twice with 1.5 ml of ether. The pellet was redissolved in 0.5 ml of 0.5M NaOH and a 250 ul aliquot taken and precipitated with 1 ml of 20% TCA. The precipitate was filtered on nitrocellulose, washed with 10% TCA and water and the filter paper measured for $^{14}C$-radioactivity. The rest of the solution was incubated at 4° C. for 24 hr. After incubation, the digest was measured for TCA-precipitable counts in exactly the same manner to determine whether any beta-elimination of glucose occurred.

5. ENZYMOLOGY OF SWEET CORN SGP

5.1 pH optima of sweet corn SGP

Most enzymes function within a limited pH range and exhibit maximal activity at a specific hydrogen ion concentration. A few operate in a broad range of pH. The sweet corn SGP not only functions over a wide range of hydrogen ion concentrations but exhibits maximal activity peaks at two separate pH values 4.5 and 8.5. In other words, the enzyme has a double pH optima. Furthermore, the enzyme is about 3 times more active at pH 8.5 than at pH 4.5.

This uncommon pH-activity curve for the sweet corn SGP, especially the difference of 4 units between the two maximal activity peaks, suggested that perhaps two separate activities were being measured. The measurements were performed with partly pure enzyme that was 80 fold purified. The sample, however, were free from any lipid-glucosylating activity and when radioglucosylated, only the 42 kDa SGP is radiolabelled. When the sample was fractionated on Sepharose C1-6B there was an enrichment of the pH 8.5 activity in the early fractions of the SGP peak suggesting that, perhaps there were two separate but similar SGP's. However, analysis of the glucosylated protein after self glucosylation at pH 4.5 and 8.5 revealed that the products, at least, were similar in that both were stable to alkali and the added glucose were removable by beta-glucosidase. When both products were analyzed by SDS-PAGE each had the same molecular weight. It appears, therefore, that there is only one SGP that has an uncommon double-pH optima. The result of the enrichment of the pH 8.5 activity in the early fractions of C1-6B remains unresolved.

5.2 Inhibition of sweet corn SGP

When a cell-free extract is assayed, an almost negligible amount of glucosylating activity is detected. The glucosylating activity is only expressed after the extract is dialyzed. Apparently a low-molecular weight inhibitor(s) is present in the extract that inhibits both the self-glucosylating protein and the lipid-glucosylating activity. Furthermore, the inhibitor is stable to heat as a heated extract inhibits the glucosylating activity in a dialyzed extract.

The endogenous inhibitor in the sweet corn extract was not identified. However, ATP was found to be a potent inhibitor to the sweet corn SGP. Rabbit muscle SGP is inhibited by ATP with 50% inhibition observed at a concentration of 3.5 mM. ATP is a 30-fold more potent inhibitor of sweet corn SGP with 50% inhibition occuring at a concentration of 100 uM.

The self-glucosylating protein in rabbit muscle is inhibited by p-nitrophenyl-saccharides, namely p-nitrophenylglucose, p-nitro-phenylmaltose, p-nitrophenylmaltotriose and p-nitrophenyl- maltotetrose. These synthetic compounds inhibit by acting as alternative substrates. The rabbit muscle SGP functions by transferring glucose from UDPglucose to a pre-existing oligosaccharide chain attached to itself via tyrosine, extending the chain to eight glucose units long. These p-nitrophenylsaccharides, by mimicking the acceptor site, can act as acceptors for the transferred glucose. In addition, this behaviour of the p-nitrophenylsaccharides further demonstrates the function of rabbit muscle SGP in synthesizing alpha-1,4 glucosidic bonds. p-Nitrophenol, p-nitrophenyl-alpha-glucoside and p-nitrophenyl-beta-glucoside were tested on sweet corn SGP and no effect on its activity was observed. This observation indicated that there was a fundamental difference in the self-glucosylating activity between the muscle and sweet corn proteins. In addition arginine and a synthetic peptide comprising the same amino acid sequence as the glucosylated tryptic peptide T2 were examined for any inhibitory effect on the activity of the sweet corn SGP. No effect was observed, indicating that the enzyme is unable to utilize these as substrates.

5.3 Dependence of sweet corn SGP on divalent cations

The muscle SGP is stimulated by manganese ions. Sweet corn SGP is completely dependent on divalent cations for its activity. When treated with EDTA the sweet corn SGP looses all its activity. The concentration dependence of sweet corn SGP on various divalent cations was measured. Manganese has the most potent stimulating effect at a concentration of 5 mM. magnesium also activated SGP but to a lesser extent than manganese, achieving a maximum stimulating effect of about 50% at 10 mM concentration. Calcium had no stimulatory effect on SGP activity.

5.4 Radioglucosylation in the absence of $MnCl_2$

When a cell-free extract is assayed for SGP in the absence of $Mn^{2+}$ ion, in addition to the SGP, a number of proteins of higher molecular weight became radiolabelled. Of these, the most prominent radiolabelled band occurs in the region of approximately 70 kDa. This form of apparent radioglucosylation occurs within the 30 min incubation period allowed for the SGP assay. The activity, however, was present only sometimes and in most preparations was absent.

A similar form of radioglucosylation has been detected with partially purified extracts (16 fold) in which proteins of molecular weight higher than SGP become radiolabelled in the absence of manganese ions. However, this form of radioglucosylation is detectable only after prolonged incubation and occurs over a 24 hr period. In addition the reaction proceeds in the presence of 1 mM $MnCl_2$ but is inhibited by 5 mM of the divalent cation. Furthermore, UDPglucose as well as ADPglucose serve as substrates for the reaction. This is unlike SGP which utilizes UDPglucose as a substrate but not ADPglucose.

The radiolabelled proteins formed during this 24 hr incubation period range in molecular weight between 42 kDa and 200 kDa and appear as sharp distinct bands on a radioautograph following SDS-electrophoresis. Evenly spaced radiolabelled bands appear between 42 kDa and 70 kDa separated by approximately 3 kDa.

The formation of these higher molecular weight products could arise from elongation of the carbohydrate component of SGP. In this case, the radiolabelled bands would represent SGP with different amounts of carbohydrate. In order to test this hypothesis, the radiolabelled products were incubated with glycogenolytic enzymes in an attempt to remove the radiolabel from the proteins. It was found that the radiolabel was resistant to hydrolysis by alpha-amylase, glucoamylase, phosphorylase and isoamylase. Consequently the radiolabelled products were incubated with cellulase to determine whether the radioactive glucose was attached in a beta-linkage. Cellulase failed to remove the radiolabel. It appears therefore that these higher molecular weight products are not starch-like or cellulose-like molecules and represents some other form of glucosylation. There is no evidence that these proteins are related to SGP.

6. PRIMING ABILITY OF SWEET CORN AMYLOGENIN (SGP)

6.1 Experimental strategy

If the sweet corn SGP was the protein primer upon which the starch molecule was constructed, then it may be possible to synthesize starch in vitro by incubating the primer with the starch synthesizing enzymes, and the glucose donor substrates (UDPglucose and ADPglucose). The synthesis of starch on the protein primer could be detected by monitoring the increase in the molecular weight of the protein as the carbohydrate increases in size. This could be accomplished by SDS-PAGE which can demonstrate any change in the molecular weight of the protein.

This approach was used to determine whether sweet corn SGP could act as a primer for the synthesis of polysaccharide. The SGP was prelabelled by allowing the protein to undergo self-glucosylation with UDP-[$^{14}$C]glucose. This permitted the detection of the protein by radioautography. Cell-free extracts of sweet corn were used as a source for the starch synthesizing enzymes. It was possible that, in addition to starch synthase and branching enzyme, other enzymes were involved in the synthesis of starch. If SGP was a primer, a 'chain extender' enzyme may be necessary to extend the single glucose into an oligosaccharide before starch synthase and branching enzyme can act.

6.2 Sweet corn SGP is a primer

The prelabelled protein, therefore, was incubated with cell-free extracts of corn and millimolar concentrations of UDPglucose and/or ADPglucose. At different time intervals aliquots of the incubation mixture were analyzed by SDS-PAGE and radioautography. After 1 hr of incubation, the appearance of a radiolabelled band at the top of the gel occurred and this was also observed for 2 hr and 3 hr time periods. In addition, there was a decrease in the amount of radiolabel at 42 kDa, the position of prelabelled SGP. The decrease in intensity of the SGP band was moreso at 2 hr and 3 hr.

The appearance of the radiolabelled band at the top of the gel could only originate from the prelabelled SGP. It appears, therefore, that the SGP was converted into a large molecular weight molecule by incubation with both UDPglucose and ADPglucose suggesting that the protein can function as a primer in polysaccharide synthesis.

6.3 Demonstration of the Priming Ability of Sweet Corn SGP

The priming ability of sweet corn SGP was examined by molecular-weight-shift experiments carried out in 3 stages.

6.3.1 Preperation of prelabelled SGP

Prelabelled SGP for this purpose was prepared from a 16 fold purified extract by incubating a sample of the enzyme with 2 uM UDP-[$^{14}$C]glucose, 5 mM $MnCl_2$ and 50 mM Tris-HCl pH 7.4 buffer at room temperature for 20 min. Following incubation, the reaction mixture was applied to a Sephadex G-25 column (6×1.5 cm) equilibrated with 50 mM Tris-HCl pH 7.4 buffer containing 2 mM CHAPS and eluted with the same buffer. Fractions (1 ml) were collected and the prelabelled SGP was detected by measuring 50 ul aliquots for $^{14}C$-radioactivity.

6.3.2 INCUBATION OF PRELABELLED SGP WITH 1 MM UDPG AND/OR ADPG

The prelabelled SGP, (typically about 10000 cpm) was incubated with 1 mM UDPglucose or 1 mM ADPglucose or both and an equal volume of dialyzed or undialyzed sweet corn extract at room temperature in 1 ml digests. At 1 hr, 2 hr, 3 hr and 24 hr time intervals 250 ul aliquots were taken and frozen to stop the reaction. The protein was precipitated with an equal volume of 20% TCA and collected by centrifugation. The pellets were washed twice with ether and dried.

6.3.3 ANALYSIS BY SDS-PAGE AND FLUOROGRAPHY

The dried pellets were dessolved in 50 ul of solubilizing buffer by incubation for 24 hr followed by strong vortexing. SDS-PAGE were performed on 10 ul of the sample followed by fluorography.

7. EXPERIMENTAL BACKGROUND TO THE INVENTION

In order to examine in detail the relationship between amylogenin and starch synthesis rate and other starch synthetic enzymes, experiments were conducted on maize plants growing under defined temperature regimes. In these experiments the maize endosperm developmentally regulated expression of amylogenin was found to parallel that of starch deposition, with minimal amylogenin activity early in endosperm development and increasing amylogenin expression as starch deposition progressed until physiological maturity of the grain.

Results demonstrated that the initiation of starch synthesis in maize endosperm is attributable to the co-ordinated expression of several enzymes involved in the pathway of starch synthesis. Continued starch deposition is dependent on a continued expression of amylogenin which acts as an important control-point in the pathway.

7.1 Developmental aspects of the formation of corn SGP in relation to starch synthesis The appearance of SGP during development must precede or coincide with the onset of starch production if the protein is a primer for starch synthesis. The formation of SGP at a later time will certainly preclude it from any involvement in the biogenesis of starch. Therefore an examination of the formation of SGP during development, particularly the period during which the polysaccharide is laid down in the cell, would provide considerable support for or against the hypothesis that the protein is a precursor of starch.

An examination of the formation of SGP and different components of the starch synthesizing system was performed on the endosperm of B73 commercial dent corn sampled at 6–30 days after pollination. The enzyme activities of SGP, ADPG pyrophosphorylase, ATP-dependent fructokinase, ATP-dependent glucokinase, branching enzyme, bound starch synthase, ATP-dependent phosphofructokinase, PPI-dependent phosphofructokinase, phosphoglucomutase, soluble starch synthase, sucrose synthase, UDPG pyrophosphorylase and UTP-dependent fructokinase were measured in terms of enzyme concentration, as units/gram dry weight and enzyme content as units/endosperm with the results expressed as a percentage of the maximum value attained. The starch content, dry weight of the endosperm, the number of endosperm cells, number of starch granules, the albumin content and concentration and the rates of starch accumulation were also measured.

It was found that SGP was already present at 6 days after pollination where other enzymes important in starch synthesis such as sucrose synthase, bound starch synthase, soluble starch synthase and branching enzyme are low in activity at this time. These enzymes reach their peak along with SGP at 10 days after pollination. The relative rate of starch accumulation is greatest between 10 and 14 days after pollination.

The appearance of SGP well before the accumulation of starch and its peak concentration occurring together with the other starch synthesizing enzymes is consistent with the protein being a precursor of starch.

7.2 Formation of SGP and enzymes involved with the starch synthesizing system during development in B73 commercial dent corn B73 commercial dent corn was harvested at different times between 6–30 days after pollination inclusively. The enzyme activities of SGP, ADPG pyrophosphorylase, ATP-dependent fructokinase, ATP-dependent glucokinase, branching enzyme, bound starch synthase, ATP-dependent phosphofructokinase, PPI-dependent phosphofructokinase, phosphoglucomutase, soluble starch synthase, sucrose synthase, UDPG pyrophosphorylase and UTP-dependent fructokinase were measured in terms of enzyme concentration, as units/endosperm. These were expressed as a percentage of the maximum value measured. In addition, the starch content, dry weight of the endosperm, the number of endosperm cells, number of starch granules, the albumin content and concentration and the rates of starch accumulation were also determined.

7.3 Purification of Prelabelled SGP from B73 Commercial Dent Corn

The isolation of prelabelled self-glucosylating protein from B73 commercial dent corn was achieved in a 800 fold purification over the cell-free extract. The protein was partially purified in an active state by successive precipitations with acid and salt followed by fractionation on DEAE-Sepharose. At this stage the 27 fold purified enzyme was allowed to undergo self-glucosylation and the prelabelled protein purified further.

The prelabelled protein was purified by successive fractionations on Sephadex S300, mono Q and $C_4$. The degree of purification and yield at each stage of the protocol is listed in Table 3.

TABLE 3

Purification of sweet corn amylogenin

| Purification Step | Specific Activity (cpm/mg protein) | Overall Yield % | Fold Purific'n |
|---|---|---|---|
| crude extract | 1750 | 100 | 1.0 |
| pH 5.0 supernatant | 2900 | 88 | 1.7 |
| 50% Ammonium Sulphate ppt | 9200 | 82 | 5.2 |
| DEAE-Sepharose | 48300 | 78 | 27.6 |
| 5300 | 140000 | 62 | 80.0 |
| Mono Q | 168000 | 53 | 96.0 |
| C4 | 1400000 | 31 | 800.0 |

The purified protein had a specific activity of $3.5 \times 10^5$ cpm/mg protein. Only 25% of the glucose, however, was radiolabelled. Therefore the calculated specific activity of the B73 corn SGP with all the incorporated glucose being radiolabelled would be $1.4 \times 10^6$ cpm /mg protein. The specific activity of the radiolabelled glucose was $4.4 \times 10^{14}$ cpm /mole of glucose. This implied that the B73 dent corn SGP had incorporated 0.13 mole of glucose into each mole of protein.

7.3 Purification of Prelabelled SGP from B73 Commercial Dent Corn

The isolation of self-glucosylating protein from B73 commercial dent corn was carried out with cobs sampled at 18 and 22 days after pollination. The protein was isolated in a prelabelled form and was achieved in two phases.

7.3.1 Phase 1

This phase of the purification was carried out in exactly the same manner as described for phase 1 in the purification of prelabelled SGP from sweet corn. The protein was partially purified and allowed to undergo autoglucosylation, 25% with UDP[$^{14}$C]glucose and the remaining 75% with unlabelled UDPglucose. The prelabelled protein was then purified further.

7.3.2 PHASE 2, PURIFICATION OF THE PRELABELLED SGP

Step 4: Fractionation by gel filtration chromatography

The prelabelling reaction mixture was applied to a Sephadex S-300 column (2×60 cm) equilibrated with 50 mM Tris-HCl pH 7.4 buffer containing 0.02% triton and eluted with the same buffer. Fractions of 3 ml each were collected and the prelabelled SGP detected by measuring 50 ul aliquots from alternating fractions for $^{14}$C-radioactivity. The fractions containing the prelabelled SGP were analyzed by SDS-PAGE and those that showed the highest protein purity were combined. The pooled fractions were concentrated by centrifugation using centriprep-10 concentrators.

Step 5: Fractionation by fast protein liquid chromatograpy (FPLC) on Mono Q

The concentrated sample was submitted to fast protein liquid chromatography (FPLC) on a Mono Q column. Protein was eluted with a linear gradient of NaCl, from 0–0.4M, formed from 50 mM Tris-HCl pH 7.4, 0.02% triton (solution A) and 50 mM Tris-HCl pH 7.4, 0.02% triton, 1.0M NaCl (solution B). The gradient was applied over a period of 40 min at a flow rate of 1 ml/min. Fractions of 1 ml were collected. The prelabelled SGP was detected by measuring the fractions for $^{14}$C-radioactivity and its purity examined by SDS-PAGE. The fractions containing the best purity were combined and concentrated.

Step 6: Fractionation by Reverse-Phase HPLC on $c_4$

The prelabelled SGP was purified next by reverse-phase HPLC using a Vydac $C_4$ column (8×40 mm). The sample was fractionated in portions of 0.16 mg each. When a larger portion containing approximately 0.32 mg was applied to the column a reduction in the resolution of the SGP containing peak was observed. Protein was eluted with a linear gradient of acetonitrile generated by using 0.1% TFA (solution A) and 0.09% TFA containing 84% acetonitrile (solution B) at a flow rate of 1 ml/min. The gradient of 0–100% solution B was applied over a period of 50 min. Protein was detected by monitoring the absorbance of the effluent at 215 nm and 295 nm simultaneously. Peaks containing protein were collected manually. The prelabelled SGP emerged from the column in a single peak.

7.4 Comparison of the properties of sweet corn SGP (amylogenin) and muscle SGP (glycogenin)

|  | sweet corn SGP | muscle SGP |
|---|---|---|
| mol. wt. (kDa) | 42 | 39 |
| tendency to aggregate | + | + |
| autocatalytic enzyme | + | + |
| cross reacts with Ab to glycogenin | + | + |
| Km for UDPglucose | similar | similar |
| stimulated by Mn2+ | + | + |
| inhibited by maltose, | − | + |
| adenine nucleotides, | + | + |
| p-nitrophenyl saccharides | − | + |
| size of carbohydrate moiety after self-glucosylation | 1 glc | 8 glc |
| configuration of glycosidic linkage | beta | alpha |
| amino acid involved in the glucosidic linkage | arginine | tyrosine |

8. GENERATION OF ANTIBODIES TO THE ENZYME

Polyclonal antibodies to purified amylogenin were generated in goats by the procedure of Lomako et al (1988, FASEB J., 2:3097–3103). Sufficient protein to enable the immunisation was obtained by pooling the enzyme subunit isolated as described above from a number of separate experiments. Antisera were prepared against the 39 kD amylogenin polypeptide. The antibodies were then tested for specificity to the amylogenin polypeptides.

The immune sera obtained precipitated amylogenin activity from crude extracts of maize endosperm. Following incubation of extracts with immune serum and centrifugation of the enzyme-Igγ-protein A-Sepharose conjugates, the amylogenin activity was detectable in the pellet fractions when the washed enzyme-Igγ-protein A-Sepharose conjugates were assayed directly for enzyme activity.

In control experiments, pre-immune sera collected from animals prior to their primary immunisation with amylogenin did not partition amylogenin activity.

Western blot analysis of total maize endosperm soluble protein using anti-maize endosperm amylogenin serum revealed the presence of a single 39 kD immunoreactive polypeptide.

Two further types of polyclonal antibody have been made. One was generated against rabbit-muscle glycogenin obtained from rabbit-muscle glycogen. The other was generated from three synthetic peptides coupled to bovine serum albumin using glutaraldehyde. The peptides were:
GDAMVTDIEAADE (SEQ ID NO:10)
REGANFVRGYPFSLR (SEQ ID NO:11)
NLDFLEMWRPFFQP (SEQ ID NO:12)

9. IDENTIFICATION OF AN AMYLOGENIN cDNA CLONE FROM MAIZE ENDOSPERM

The antibodies produced above may be used to screen a maize endosperm cDNA library for clones derived from the mRNAs for amylogenin in an in vitro transcription/translation system.

The cDNA library may also be screened with oligonucleotide sequences derived from the amino acid sequence of amylogenin. Numerous oligonucleotide probes have been synthesised.

An amplified maize endosperm cDNA library has been constructed. Double-stranded cDNA was prepared from oligo dT-cellulose-purified maize endosperm RNA by a method employing RNaseH and *E coli* DNA polymerase for the synthesis of the second strand, without prior purification of single-stranded cDNA (Gubler and Hoffman, 1983). The antibody and oligonucleotide probes are used to screen this library to identify clones containing cDNA encoding maize endosperm amylogenin.

Clones producing strong positive signals are plaque-purified during additional rounds of screening. DNA is prepared from the putative maize endosperm amylogenin cDNA clones. Following restriction endonuclease digestion of the DNAs with EcoR1 and agarose gel electrophoresis, the sizes of the cDNA inserts of these clones are determined. The cDNA insert is labelled with $^{32}P$ by nick-translation and used to probe a northern blot of poly(A)-containing RNA from maize endosperm. The size of the mRNA bands to which this probe hybridises indicates the size of the maize endosperm amylogenin mRNA. This should be in close agreement with the estimates from western blots of maize endosperm amylogenin.

9.1 Molecular cloning of the amylogenin cDNA

An amplified cDNA library ($10^6$ plaque-forming units/ml) from corn endosperm constructed on lambda ZAPII was used as the DNA template for PCR. A sense primer (SEQ ID NO:13)CC(T/C/A/G)TTCTTCTT(C/T)AA(C/T)AC was designed from the partial amino acid sequence of the protein while the antisense primer (SEQ ID NO:14), TCGACGGTATCGATAAGC, was from lambda ZAPII nucleotide sequence. After 30 cycles (95° C. for 1 min; 45° C. for 2 min and 72° C. for 2 min followed by a final extension step for 6 min at 72° C.), the PCR product was cloned into a PCR 1000 vector (invitrogen) and sequenced using Sequenase Version 2.0 (USB). A probe about 500 base pairs in length was obtained containing the deduced sequence for three peptides already sequenced directly. Digoxigenin was then incorporated into the cloned fragment as digoxigenin-11-dUPT by means of PCR, using the modified nucleotide in a 1:2 ratio with dTTP. This served as a probe for screening the cDNA library. Approximately $10^6$ plaque-forming units of lambda ZAPII phage were used to infect E coli strain XL1-Blue (Stratagene) and after plating the plaques were transferred to nylon membranes in duplicate. The hybridisation buffer contained 5×SSC (chloride-citrate), 0.5% blocking reagent (Boehringer), 0.1% N-laurylsarcosine, 0.02% SDS and 15 ng/ml of DNA probe.

After overnight hybridisation at 65° C., the membranes were washed with 0.5×SSC and 0.1% SDS at 65° C. Putative positive clones were detected by the Genius kit (Boehringer), subjected to three additional rounds of purification and excised from lambda ZAPII to yield recombinant pBluescript phagemid carrying ampicillin resistance, using ExAssist helper phage in the in vivo excision protocol provided by Stratagene, which utilises the E coli SOLR strain.

10. SEQUENCE ANALYSIS OF THE AMYLOGENIN cDNA CLONES

The cDNA insert from each clone may be sequenced using standard techniques.

Each clone will encode a polypeptide equivalent to a partial or a complete amylogenin protein. The hydropathy index (Kyte and Doolittle, 1982) and secondary structure predictions (Chou and Fasman, 1978) may be calculated for the encoded protein using the programmes of Devereux et al (1987). The Kyte and Doolittle (1982) hydropathy profile indicates the hydrophobic and hydrophilic domains within the protein and should be consistent with its location in the cell (Kaiser and Bassham, 1979). The secondary structure predictions of Chou and Fasman (1978) may be used in comparisons of the maize endosperm and animal glycogenin and/or amylogenin proteins.

The various amylogenin and/or glycogenin cDNA sequences may be compared to indicate the extent of homology. A detailed comparison of the nucleotide sequences of the cDNA will identify base substitutions, insertions or deletions, and hence the amino acid changes produced in the derived protein sequences.

One amylogenin cDNA clone has been sequenced by the dideoxy method using Sequenase Version 2.0 DNA Sequencing Kit (USB). The cDNA clone encoding amylogenin was deposited at the American Type Culture Collection, 12301 Parklawn Drive, Rockville, Md. 20852, U.S.A. under the terms of the Budapest Treaty on 19 Aug. 1993 under the accession number ATCC 69389.

Partial cDNA sequences corresponding to amylogenin from B73 maize are given below in Tables 4 and 5. These match-up with the amino acid sequences of some of the peptide fragments shown above.

TABLE 4

| SEQUENCE (I) (SEQ ID NO: 15) |
|---|
| TGAACTTGGCCTTTGACCGTGAGCTCATTGGTCCGGCTATGTACTTCGGTC TCCTGGGTGATGGTCAGCCTATTGGTCGCTACGACGATATGTGGGCTGGGT GGTGTGTCAAGGTGATCTGTGATCATTTGGGATTGGGAGTGAAGACGGGTC TTCCCTACATCTACCACAGCAAGGCGAGCAACCCATTTGTGAACCTGAAGA AGGAGTACAAGGGAATTTTCTGGCAGGAGGACATCATGCCTTTCTTCCAGA GTGCAAAGCTCTCGAAAGAAGCTGTGACGGTTCAACAATGCTACATTGAGC TGTCCAAGATGGTGAAGGAGAAGCTTAGCGCCATTGATCCTTACTTTGACA AGCTTGCTGATGCTATGGTGACTTGGATTGACGCTTGGGATGTGCTTAACC CGGCCACATAAG |

TABLE 5

| SEQUENCE (II) (SEQ ID NO: 16) |
|---|
| CTTCCGTTCTTCTTTAACACCTTGTACGATCCCTACCGTGAAGGTGCTGAC TTCGTCCGTGGATACCCTTTCAGTCTCCGTGAGGGTGTTTCCACTGCTGTT TCTCACGGTCTCGGGCTCAACATCCCTGATTACGACGCCCCAACTCAACTC GTCAAGCCTAAGGAAAGAAACACAAGGTATGTGGATGCTGTCATGACCATC CCAAAGGAACACCTTTGGCCAATTGTGTGGCATGAACTGCC |

The cDNA clones may also be compared by restriction mapping. Restriction maps of the maize endosperm amylogenin cDNAs are constructed to demonstrate their relatedness.

Sequences may also be compared to other glycogenin and/or amylogenin polypeptides. For example, the amino acid sequences derived from the maize amylogenin cDNAs may be aligned with the amino acid sequences derived from an animal glycogenin cDNA (Cohen et al, 1990). The homologies between amino acid sequences are subsequently calculated on the basis of this alignment.

11. IDENTIFICATION OF A MAIZE ENDOSPERM AMYLOGENIN gDNA CLONE

The cDNAs derived as above may be used to probe a maize genomic library to isolate maize amylogenin genomic DNAs.

In addition, the oligonucleotide probes generated from the amylogenin N-terminal amino acid sequence information may be used to screen the maize genomic library.

12. CONSTRUCTION OF TRANSFORMATION CASSETTE

The glycogenin and/or amylogenin gene transformation construct requires the presence of an amyloplast transit peptide to ensure its correct localisation in the amyloplast. It is believed that chloroplast transit peptides have similar sequences but other potential sources are available such as that attached to ADPG pyrophosphorylase (Plant Mol Biol Reporter, 1991, 9:104–126). Other potential transit peptides are those of small subunit RUBISCO, acetolactate synthase, glyceraldehyde-3P-hydrogenase and nitrite reductase. For example, consensus sequence of the transit peptide of small subunit RUBISCO from many genotypes has the sequence (SEQ ID NO:17): MASSMLSSAAV—ATRTNPAQAS MVAPFTGLKSAAFPVSRK QNLDITSIA SNGGRVQC;

the corn small subunit RUBISCO has the sequence (SEQ ID NO:18): MAPTVMMASSAT-ATRTNPAQAS AVAPFQGLKSTASLPVARR SSRSLGNVA SNGGR-IRC;

the transit peptide of leaf starch synthase from corn has the sequence (SEQ ID NO:19): MA ALATSQLVAT RAGLGVPDAS TFRRGAAQGL RGARASAAAD TLSMRTASARA APRHQQQARR GGRFPSLVVC;

the transit peptide of leaf glyceraldehyde-3P-dehydrogenase from corn has the sequence (SEQ ID NO:20): MAQILAPS TQWQNRITKT SPCATPITSK MWSSLVMKQT KKVAHSAKFR VMAVNSENGT;

the putative transit peptide from ADPG pyrophosphorylase from wheat has the sequence (SEQ ID NO:21): RASPPSESRA PLRAPQRSAT RQHQARQGPR RMC.

It is possible to express the glycogenin and/or amylogenin enzyme constitutively using one of the well-known constitutive promoters such as CaMV35S but there may be biochemical penalties in the plant resulting from increased starch deposition throughout the entire plant. Deposition in the endosperm is preferred. Possible promoters for use in the invention include the promoters of the starch synthase gene, ADPG pyrophosphorylase gene, and the sucrose synthase gene.

13. INSERTION OF GLYCOGENIN AND/OR AMYLOGENIN DNA INTO MAIZE

The glycogenin and/or amylogenin DNA may be transformed into either protoplasts or other tissues of a maize inbred line or population. The existing gene promoters in genomic DNA ensure that the extra genes are expressed only in the developing endosperm at the correct developmental time. The protein sequences likewise ensure that the enzymes are inserted into the amyloplast.

14. TRANSGENIC PLANTS AND PROGENY

Transgenic maize plants are regenerated and the endosperms of these plants are tested for increased glycogenin and/or amylogenin enzyme activity. The kernels are also tested for enhanced rate of starch synthesis at different temperatures, starch yield, etc.

The plants are then included in a breeding program to produce new maize hybrids with altered starch synthesis.

---

We claim:

1. An isolated nucleic acid molecule comprising a nucleotide sequence encoding a polypeptide having amylogenin activity wherein said polypeptide is encoded by a plant gene and wherein said nucleotide sequence hybridizes at 65° C. in 5xSSC to a DNA probe selected from the group consisting of: a DNA having the complement of the sequence in Table 4 (SEQ ID NO:15), a DNA having the complement of the sequence in Table 5 (SEQ ID NO:16) and a DNA having the complement of the sequence encoding the polypeptide having amylogenin activity of the maize cDNA clone contained in the deposit at the American Type Culture Collection under the accession number ATCC 69389.

2. An isolated nucleic acid molecule of claim 1, wherein said plant is selected from the group consisting of: *Zea mays, Zea diploperennis, Zea luxurians, Zea perennis, Zea tripsacum, Zea parviglumis, Zea mexicana,* and teosinte.

3. An isolated nucleic acid molecule comprising a nucleotide sequence encoding a polypeptide having amylogenin activity wherein said polypeptide is encoded by a maize gene.

4. An isolated nucleic acid molecule according to claim 3 wherein said nucleotide sequence is selected from the group consisting of:

(a) a nucleotide sequence comprising the nucleotide sequence in Table 4 (SEQ ID NO 15) or the nucleotide sequence in Table 5 (SEQ ID NO 16);

(b) a nucleotide sequence encoding the polypeptide having amylogenin activity which is encoded by the nucleotide sequence in Table 4 (SEQ ID NO 15) or the nucleotide sequence in Table 5 (SEQ ID NO 16);

(c) a nucleotide sequence comprising the nucleotide sequence of the maize cDNA clone contained in the deposit at the American Type Culture Collection under the accession number ATCC 69389;

(d) a nucleotide sequence encoding the polypeptide having amylogenin activity which is encoded by the maize cDNA clone contained in the deposit at the American Type Culture Collection under the accession number ATCC 69389;

(e) a nucleotide sequence encoding a polypeptide having amylogenin activity wherein said polypeptide comprises an amino acid sequence selected from the group consisting of: SEQ ID NO:1; SEQ ID NO:2; SEQ ID NO:3; SEQ ID NO:4; SEQ ID NO:5; SEQ ID NO:6; SEQ ID NO:7; SEQ ID NO:8; and SEQ ID NO:9; and (f) a nucleic acid molecule which hybridizes at 65° C. in 5xSSC to a DNA probe selected from the group consisting of: a DNA having the complement of the sequence in Table 4 (SEQ ID NO:15); a DNA having the complement of the sequence in Table 5 (SEQ ID NO:16); and a DNA having the complement of the sequence encoding the polypeptide having amylogenin activity of the maize cDNA clone contained in the deposit at the American Type Culture Collection under the accession number ATCC 69389.

5. An isolated nucleic acid molecule according to claim 4 wherein said nucleotide sequence is a nucleotide sequence encoding the polypeptide having amylogenin activity which is encoded by the maize cDNA clone contained in the deposit at the American Type Culture Collection under the accession number ATCC 69389.

6. An isolated nucleic acid molecule comprising a nucleotide sequence which is the complement of the nucleotide sequence of the nucleic acid molecule of claim 1.

7. An isolated nucleic acid molecule comprising a nucleotide sequence which is the complement of the nucleotide sequence of the nucleic acid molecule of claim 3.

8. A plant or progeny thereof each stably transformed by a nucleic acid molecule according to claim 1.

9. A plant or progeny thereof each stably transformed by a nucleic acid molecule according to claim 3.

10. A plant or progeny thereof each stably transformed by a nucleic acid molecule according to claim 6.

11. A plant or progeny thereof each stably transformed by a nucleic acid molecule according to claim 7.

12. A seed of a plant according to claim 8.

13. A seed of a plant according to claim 9.

14. A seed of a plant according to claim 10.

15. A seed of a plant according to claim 11.

16. A plant according to claim 8, wherein said plant is of the family Graminae.

17. A plant according to claim 16, wherein said plant is of the species *Zea mays*.

18. A plant according to claim 8, wherein said plant is a tomato.

19. A plant according to claim 8, wherein the genome of said plant is homozygous for the sequence of said nucleic acid molecule.

20. A hybrid plant wherein at least one parent of said hybrid plant is a plant according to claim 8.

21. A plant or progeny thereof each stably transformed by a nucleic acid molecule comprising a nucleotide sequence encoding a polypeptide having glycogenin activity wherein said polypeptide is encoded by an animal gene.

22. A plant according to claim 21 wherein said polypeptide is encoded by a rabbit gene.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Tyr  Val  Asn  Ala  Val  Met  Thr  Ile  Pro  Lys
 1                    5                        10
```

( 2 ) INFORMATION FOR SEQ ID NO:2:

( i ) SEQUENCE CHARACTERISTICS:
        ( A ) LENGTH: 14 amino acids
        ( B ) TYPE: amino acid (C) STRANDEDNESS: single
            (D) TOPOLOGY: linear (ii) MOLECULE TYPE: peptide (xi) SEQUENCE DESCRIPTION: SEQ ID NO:2:

Glu Gly Ala Asn Phe Val Xaa Gly Tyr Pro Phe Ser Leu Arg
    1               5                   10

(2) INFORMATION FOR SEQ ID NO:3:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Tyr Xaa Xaa Met Trp Ala Gly Trp Thr Val Lys
    1               5                   10

(2) INFORMATION FOR SEQ ID NO:4:

(i) SEQUENCE CHARACTERISTICS:
            (A) LENGTH: 28 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Glu Gly Ala His Thr Ala Val Ser His Gly Leu Trp Leu Asn Ile Pro
    1               5                   10                  15

Asp Tyr Asp Ala Pro Thr Gln Leu Val Lys Pro Lys
                20                  25

(2) INFORMATION FOR SEQ ID NO:5:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Leu Gly Asp Ala Met Val Thr Trp Ile Glu Ala Trp Asp Glu Leu Asn
    1               5                   10                  15

Pro Ser Thr Pro Ala Ala Ala Asp Gly Lys
                20                  25

(2) INFORMATION FOR SEQ ID NO:6:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Leu Gly Asp Ala Met Val Thr Asp Ile Glu Ala Ala Asp Glu Leu Asn
    1               5                   10                  15

Pro Ala Gly Pro Xaa Xaa Xaa Xaa Lys
                         20                          25

( 2 ) INFORMATION FOR SEQ ID NO:7:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Asn Leu Leu Ser Pro Ser Thr Pro Phe Phe Phe Asn Thr Leu Tyr Asp
        1               5                   10                  15

Pro Tyr Arg Glu Gly Ala Asn Phe Val Xaa Gly Tyr Pro Phe Ser Leu
                        20                  25                  30

Arg ( 2 ) INFORMATION FOR SEQ ID NO:8:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Gly Ile Phe Trp Gln Glu Asp Ile Ile Pro Phe Phe Gln Asn Val Thr
        1               5                   10                  15

Ile Pro Lys ( 2 ) INFORMATION FOR SEQ ID NO:9:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Asn Leu Asp Phe Leu Glu Met Trp Arg Pro Phe Phe Gln Pro Tyr His
        1               5                   10                  15

Leu Ile Ile Val Gln Asp Gly Asp Pro Thr Lys
                        20                  25

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Gly Asp Ala Met Val Thr Asp Ile Glu Ala Ala Asp Glu
        1               5                   10

( 2 ) INFORMATION FOR SEQ ID NO:11:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Arg Glu Gly Ala Asn Phe Val Arg Gly Tyr Pro Phe Ser Leu Arg
1               5                   10                  15

( 2 ) INFORMATION FOR SEQ ID NO:12:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Asn Leu Asp Phe Leu Glu Met Trp Arg Pro Phe Phe Gln Pro
1               5                   10

( 2 ) INFORMATION FOR SEQ ID NO:13:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid ( i v ) ANTI-SENSE: NO ( x i ) SEQUENCE DESCRIPTION: SEQ ID NO:13:

CCNTTCTTCT TYAAYAC                                                                           17

( 2 ) INFORMATION FOR SEQ ID NO:14:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid ( i v ) ANTI-SENSE: YES ( x i ) SEQUENCE DESCRIPTION: SEQ ID NO:14:

TCGACGGTAT CGATAAGC                                                                          18

( 2 ) INFORMATION FOR SEQ ID NO:15:

( i ) SEQUENCE CHARACTERISTICS:
    ( A ) LENGTH: 420 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: NO ( x i ) SEQUENCE DESCRIPTION: SEQ ID NO:15:

TGAACTTGGC CTTTGACCGT GAGCTCATTG GTCCGGCTAT GTACTTCGGT CTCCTGGGTG                             60

| ATGGTCAGCC | TATTGGTCGC | TACGACGATA | TGTGGGCTGG | GTGGTGTGTC | AAGGTGATCT | 120 |
| GTGATCATTT | GGGATTGGGA | GTGAAGACGG | GTCTTCCCTA | CATCTACCAC | AGCAAGGCGA | 180 |
| GCAACCCATT | TGTGAACCTG | AAGAAGGAGT | ACAAGGGAAT | TTTCTGGCAG | GAGGACATCA | 240 |
| TGCCTTTCTT | CCAGAGTGCA | AAGCTCTCGA | AAGAAGCTGT | GACGGTTCAA | CAATGCTACA | 300 |
| TTGAGCTGTC | CAAGATGGTG | AAGGAGAAGC | TTAGCGCCAT | TGATCCTTAC | TTTGACAAGC | 360 |
| TTGCTGATGC | TATGGTGACT | TGGATTGACG | CTTGGGATGT | GCTTAACCCG | GCCACATAAG | 420 |

(2) INFORMATION FOR SEQ ID NO:16:

(i) SEQUENCE CHARACTERISTICS:
        (A) LENGTH: 245 base pairs
        (B) TYPE: nucleic acid
        (C) STRANDEDNESS: single
        (D) TOPOLOGY: linear (ii) MOLECULE TYPE: cDNA (iv) ANTI-SENSE: NO (xi) SEQUENCE DESCRIPTION: SEQ ID NO:16:

| CTTCCGTTCT | TCTTTAACAC | CTTGTACGAT | CCCTACCGTG | AAGGTGCTGA | CTTCGTCCGT | 60 |
| GGATACCCTT | TCAGTCTCCG | TGAGGGTGTT | TCCACTGCTG | TTTCTCACGG | TCTCGGGCTC | 120 |
| AACATCCCTG | ATTACGACGC | CCCAACTCAA | CTCGTCAAGC | CTAAGGAAAG | AAACACAAGG | 180 |
| TATGTGGATG | CTGTCATGAC | CATCCCAAAG | GAACACCTTT | GGCCAATTGT | GTGGCATGAA | 240 |
| CTGCC | | | | | | 245 |

(2) INFORMATION FOR SEQ ID NO:17:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Met Ala Ser Ser Met Leu Ser Ser Ala Ala Val Xaa Xaa Ala Thr Arg
 1               5                  10                  15

Thr Asn Pro Ala Gln Ala Ser Met Val Ala Pro Phe Thr Gly Leu Lys
            20                  25                  30

Ser Ala Ala Phe Pro Val Ser Arg Lys Gln Asn Leu Asp Ile Thr Ser
        35                  40                  45

Ile Ala Ser Asn Gly Gly Arg Val Gln Cys
    50                  55
```

(2) INFORMATION FOR SEQ ID NO:18:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Met Ala Pro Thr Val Met Met Ala Ser Ser Ala Thr Xaa Ala Thr Arg
 1               5                  10                  15

Thr Asn Pro Ala Gln Ala Ser Ala Val Ala Pro Phe Gln Gly Leu Lys
            20                  25                  30
```

Ser  Thr  Ala  Ser  Leu  Pro  Asn  Ala  Arg  Arg  Ser  Ser  Arg  Ser  Leu  Gly
                          35                       40                      45

Asn  Val  Ala  Ser  Asn  Gly  Gly  Arg  Ile  Arg  Cys
                          50                       55

(2) INFORMATION FOR SEQ ID NO:19:

(i) SEQUENCE CHARACTERISTICS:
      (A) LENGTH: 73 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:19:

Met  Ala  Ala  Leu  Ala  Thr  Ser  Gln  Leu  Val  Ala  Thr  Arg  Ala  Gly  Leu
                 1                   5                       10                      15

Gly  Val  Pro  Asp  Ala  Ser  Thr  Phe  Arg  Arg  Gly  Ala  Ala  Gln  Gly  Leu
                          20                       25                      30

Arg  Gly  Ala  Arg  Ala  Ser  Ala  Ala  Ala  Asp  Thr  Leu  Ser  Met  Arg  Thr
                          35                       40                      45

Ala  Ser  Ala  Arg  Ala  Ala  Pro  Arg  His  Gln  Gln  Gln  Ala  Arg  Arg  Gly
                          50                       55                      60

Gly  Arg  Phe  Pro  Ser  Leu  Val  Val  Cys
                 65                      70

(2) INFORMATION FOR SEQ ID NO:20:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:20:

Met  Ala  Gln  Ile  Leu  Ala  Pro  Ser  Thr  Gln  Trp  Gln  Met  Arg  Ile  Thr
                 1                   5                       10                      15

Lys  Thr  Ser  Pro  Cys  Ala  Thr  Pro  Ile  Thr  Ser  Lys  Met  Trp  Ser  Ser
                          20                       25                      30

Leu  Val  Met  Lys  Gln  Thr  Lys  Lys  Val  Ala  His  Ser  Ala  Lys  Phe  Arg
                          35                       40                      45

Val  Met  Ala  Val  Asn  Ser  Glu  Asn  Gly  Thr
                          50                       55

(2) INFORMATION FOR SEQ ID NO:21:

(i) SEQUENCE CHARACTERISTICS:
      (A) LENGTH: 33 amino acids
      (B) TYPE: amino acid
      (C) STRANDEDNESS: single
      (D) TOPOLOGY: linear (ii) MOLECULE TYPE: peptide -continued (xi) SEQUENCE DESCRIPTION: SEQ ID NO:21:

Arg Ala Ser Pro Pro Ser Glu Ser Arg Ala Pro Leu Arg Ala Pro Gln
 1               5                   10                      15

Arg Ser Ala Thr Arg Gln His Gln Ala Arg Gln Gly Pro Arg Arg Met
                20                   25                      30

Cys